(12) United States Patent
Mayes et al.

(10) Patent No.: US 8,796,303 B2
(45) Date of Patent: Aug. 5, 2014

(54) IMIDAZO[2,1-G][1,7]NAPHTHYRIDINES FOR TREATING RESPIRATORY SYNCYTIAL VIRUS INFECTIONS

(75) Inventors: Penelope Anne Mayes, Notting Hill (AU); Jeffrey Peter Mitchell, Notting Hill (AU); Alistair George Draffan, Notting Hill (AU); Gary Robert William Pitt, Notting Hill (AU); Kelly Helen Anderson, Notting Hill (AU); Chin Yu Lim, Notting Hill (AU)

(73) Assignee: Biota Scientific Management Pty Ltd., Victoria (AU)

( * ) Notice: Subject to any disclaimer, the term of this patent is extended or adjusted under 35 U.S.C. 154(b) by 0 days.

(21) Appl. No.: 13/302,975

(22) Filed: Nov. 22, 2011

(65) Prior Publication Data

US 2012/0135998 A1 May 31, 2012

Related U.S. Application Data

(60) Provisional application No. 61/417,347, filed on Nov. 26, 2010.

(30) Foreign Application Priority Data

Nov. 26, 2010 (AU) ............................... 2010905234

(51) Int. Cl.
| | | |
|---|---|---|
| *A61K 31/42* | (2006.01) | |
| *A61K 31/4375* | (2006.01) | |
| *C07D 261/06* | (2006.01) | |
| *C07D 487/12* | (2006.01) | |

(52) U.S. Cl.
USPC .............. 514/293; 514/471; 546/94; 548/248

(58) Field of Classification Search
CPC . A61K 31/42; A61K 31/4375; C07D 261/06; C07D 487/12
USPC ....................... 514/293, 471; 546/94; 548/248
See application file for complete search history.

(56) References Cited

U.S. PATENT DOCUMENTS

| | | |
|---|---|---|
| 3,311,629 A | 3/1967 | Sulkowski |
| 3,379,733 A | 4/1968 | Houlihan |
| 3,507,863 A | 4/1970 | Houlihan |
| 3,590,043 A | 6/1971 | Graf |
| 3,624,101 A | 11/1971 | Sulkowski et al. |
| 3,657,221 A | 4/1972 | Sulkowski et al. |
| 3,770,766 A | 11/1973 | Sulkowski et al. |
| 3,885,037 A | 5/1975 | Sulkowski |
| 3,935,218 A | 1/1976 | Sulkowski |
| 3,966,955 A | 6/1976 | Shriver et al. |
| 4,056,536 A | 11/1977 | Atkinson et al. |
| 4,058,529 A | 11/1977 | Graf et al. |
| 4,565,566 A | 1/1986 | Draber et al. |
| 4,701,208 A | 10/1987 | Los |
| 4,717,414 A | 1/1988 | Hunt |
| 4,726,838 A | 2/1988 | Dürr et al. |
| 4,741,767 A | 5/1988 | Obrecht |
| 4,785,002 A | 11/1988 | Draber et al. |
| 4,846,876 A | 7/1989 | Draber et al. |
| 5,329,006 A | 7/1994 | Baumann et al. |
| 5,426,192 A | 6/1995 | Baumann et al. |
| 5,512,564 A | 4/1996 | Zilch et al. |
| 2007/0287700 A1 | 12/2007 | Bond et al. |
| 2010/0021458 A1 | 1/2010 | Mitchell et al. |

FOREIGN PATENT DOCUMENTS

| | | |
|---|---|---|
| CA | 2104963 | 2/1992 |
| CA | 2108899 | 3/1992 |
| CH | 481124 | 9/1966 |
| CH | 482697 | 3/1967 |
| EP | 1207161 | 5/2002 |
| GB | 1038735 | 8/1966 |
| GB | 1105219 | 9/1966 |
| GB | 1059175 | 2/1967 |
| GB | 1229651 | 4/1971 |
| GB | 1322339 | 7/1973 |
| WO | WO 92/13863 | 8/1992 |
| WO | WO 92/16207 | 10/1992 |
| WO | WO 01/95910 | 5/2001 |
| WO | WO 02/26228 | 4/2002 |
| WO | WO 02/42326 | 5/2002 |

(Continued)

OTHER PUBLICATIONS

Evans et al., "Viral Infections of Humans," *Epidemiology and Control*, 3rd Edition, Plenum Medical Book, New York, pp. 525-544, 1989.

Stephenson, "New HIV prevention strategies urged," *JAMA* 292(10):1163-1164, 2004.

Non-Final Office Action from corresponding U.S. Appl. No. 12/443,177 dated Oct. 29, 2012.

Non-Final Office Action from corresponding U.S. Appl. No. 13/023,473 dated Oct. 30, 2012.

(Continued)

*Primary Examiner* — Douglas M Willis
(74) *Attorney, Agent, or Firm* — B. Aaron Schulman, Esq.; Stites & Harbison, PLLC.

(57) ABSTRACT

The present invention relates to compounds of formula (I), racemates, isomers and/or salts thereof useful in the treatment of viral infections, in particular respiratory syncytial virus (RSV) infections. The present invention also relates to processes for preparing the compounds.

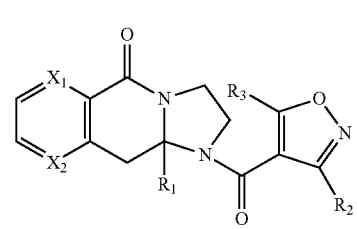

24 Claims, No Drawings

(56) References Cited

FOREIGN PATENT DOCUMENTS

| | | |
|---|---|---|
| WO | WO 02/066479 | 8/2002 |
| WO | WO 03/040178 | 5/2003 |
| WO | WO 2005/061513 | 7/2005 |
| WO | WO 2006/116764 | 11/2006 |
| WO | WO 2008/037011 | 4/2008 |

OTHER PUBLICATIONS

Aeberli et al., "Anorectic Agents. 2. Structural Analogs of 5-(p-Chlorophenyl)-2,3-dihydro-5H-imidazo[2,1-α]isoindol-5-ol," *Journal of Medicinal Chemistry* 18(2):182-185, 1975.

Aeberli et al., "5-Aryl-2,3-dihydro-5H-imidazo[2,1-α]isoindol-5-ols. A Novel Class of Anorectic Agents," *Journal of Medicinal Chemistry* 28(2):177-182, 1975.

Aeberli et al., "The Lithium Aluminum Hydride Reduction Products from Heterocycles Containing an Isoindolone Nucleus," *The Journal of Organic Chemistry* 34(6):1722-1726, Jun. 1969.

Ames et al., "Heterocyclic Synthesis from o-Halogeno-acids. Part III. Synthesis of 2-Methylindole-4-carboxylic Acid and Related Compounds and of Some Derivatives of 3-Phenylisoquinolin-1(2H)-one," *J. Chem. Society* 1073-1078, 1976.

Black, "Systematic Review of the Biology and Medical Management of Respiratory Syncytial Virus Infection," *Respiratory Care* 48(3):209-233, Mar. 2003.

Bruggink et al., "A study of the copper-catalysed direct arylation β-dicarbonyl compounds with 2-bromobenzoic acids," *Tetrahedron* 31:2607-2619, 1975.

Cianci et al., "Orally Active Fusion Inhibitor of Respiratory Syncytial Virus," *Antimicrobial Agents and Chemotherapy* 48(2):413-422, Feb. 2004.

Epsztajn et al., "Application of Organolithium and Related Reagents in Synthesis. Part II. Metallation of 2-Methyl- and 4-Methylnicotinic Acids. A Useful Method for Preparation of Aza-Isocoumarins," *Synthetic Compounds* 22(9): 1239-1247, 1992.

Falsey, "Noninfluenza Respiratory Virus Infection in Long-Term Care Facilities," *Infection Control and Hospital Epidemiology* 12:602-608, 1991.

Garvie et al., "Outbreak of respiratory syncytial virus infection in the elderly," *Br. Med. J.* 281:1253-1254, 1980.

Guion et al., "The Preparation of 2-(2-OXO-2-Phenylethyl)Benzoic Acids From Dilithiated *Ortho*-Toluic Acid," *Synthetic Compounds* 26(9):1753-1762, 1996.

Hall et al., "Aerosolized Ribavirin Treatment of Infants with Respiratory Syncytial Viral Infection," *The New England Journal of Medicine* 308(24):1443-1447, Jun. 1983.

Hall et al., "Ribavirin Treatment of Respiratory Syncytial Viral Infection in Infants with Underlying Cardiopulmonary Disease," *JAMA* 254(21):3047-3051, Dec. 1985.

Hertz et al., "Respiratory Syncytial Virus-Induced Acute Lung Injury in Adult Patients with Bone Marrow Transplants: A Clinical Approach and Review of the Literature," *Medicine* 68(5):269-281, 1989.

Katritzky et al., "Convenient syntheses of dihydropyrrolo[2',1':3,4]pyrazino- and dihydropyrrolo[2'1,1':3,4][1,4]diazepino-[2,1-α]isoindolones," *Tetrahedron Letters* 43:2831-2833, 2002.

Katritzky et al., "Stereoselective syntheses of chiral (3S,9bS)-1,2,3,9b-tetrahydro-5H-imidazo[2,1-60 ]isoindo1-5-ones," *Tetrahedron: Asymmetry* 13:933-938, 2002.

Kruse et al., "Some Benzyl-Substituted Imidazoles, Triazoles, Tetrazoles, Pyridinethiones, and Structural Relatives as Multisubstrate Inhibitors of Dopamine β-Hydroxylase. 4. Structure-Activity Relationships at the Copper Binding Site," *J. Med. Chem.* 33:781-789, 1990.

Metlesics et al., "The Structure of the Reaction Product of o-Benzoylbenzoic Acid with Ethylenediamine," *Journal of Organic Chemistry* 32:2185-2187, 1967.

Morton et al., "Structural characterization of respiratory syncytial virus fusion inhibitor escape mutants: homology model of the F protein and a syncytium formation assay," *Virology* 311:275-288, 2003.

Mufson et al., "Two Distinct Subtypes of Human Respiratory Syncytial Virus," *J. Gen. Virol.* 66:211-2124, 1985.

Natsugari et al., "Novel, Potent, and Orally Active Substance P Antagonists: Synthesis and Antagonist Activity of N-Benzylcarboxamide Derivatives of Pyrido[3,4-b]pyridine," *J. Med. Chem.* 38:3106-3120, 1995.

Prasad et al., "18-Crown-6 as a Catalyst in the Dialkylation of o-Nitrophenacyl Derivatives," *J. Org. Chem.* 56:7188-7190, 1991.

Sulkowski et al., "2,5-Benzodiazocines and Intermediates," *Journal of Organic Chemistry* 32:2180-2184, 1967.

Van den Hoogen et al., "A newly discovered human pneumovirus isolated from young children with respiratory tract disease," *Nat. Med.* 7(6):719-724, Jun. 2001.

Van den Hoogen et al., "Analysis of the Genomic Sequence of a Human Metapneumovirus," *Virology* 295:119-132, 2002.

Van den Hoogen et al., "Clinical impact and diagnosis of human metapneumovirus infection," *Pediatr. Infect. Dis. J.* 23:S25-32, 2004.

Van den Hoogen et al., "Prevalence and Clinical Symptoms of Human Metapneumovirus Infection in Hospitalized Patients," *J Infect. Dis.* 188:1571-1577, 2003.

Watanabe et al., "MTT colorimetric assay system for the screening of anti-orthomyxo- and anti-paramyxoviral agents," *Journal of Virological Methods* 48:257-265, 1994.

Wyde et al., "Short duration aerosols of JNJ 2408068 (R170591) administered prophylactically of therapeutically protect cotton rats from experimental respiratory syncytial virus infection," *Antiviral Research* 60:221-231, 2003.

Yamaguchi et al., "Novel Antiasthmatic Agents with Dual Activities of Thromboxane $A_2$ Synthetase Inhibition and Bronchodilation. 1. 2-[2-(1-Imidazoly)alkyl]-1(2H)-phthalazinones," *J. Med. Chem.* 36:4052-4060, 1993.

Non-Final Office Action dated May 26, 2010, from U.S. Appl. No. 10/585,230.

Final Office Action dated Dec. 8, 2010, from U.S. Appl. No. 10/585,230.

Non-Final Office Action dated Apr. 20, 2011, from U.S. Appl. No. 12/443,177.

Final Office Action dated Nov. 8, 2011, from U.S. Appl. No. 12/443,177.

IMIDAZO[2,1-G][1,7]NAPHTHYRIDINES FOR TREATING RESPIRATORY SYNCYTIAL VIRUS INFECTIONS

CROSS-REFERENCE TO RELATED APPLICATION

This application claims the benefit of priority of U.S. Provisional Application No. 61/417,347, filed Nov. 26, 2010, and Australia Application No. 2010905234, filed Nov. 26, 2010, both of which are herein incorporated by reference in their entirety.

TECHNICAL FIELD

The present invention relates to compounds useful in the treatment of viral infections, in particular respiratory syncytial virus (RSV) infections. The present invention also relates to processes for preparing the compounds.

BACKGROUND

Respiratory syncytial virus (RSV) is the leading cause of acute upper and lower respiratory tract infections (LRTI) in adults, young children and infants. Although at risk populations include the hospitalised, elderly and high-risk adults, RSV is primarily considered to be a paediatric disease due to the prevalence and severity of unfavourable outcomes in infants. Acute LRTI are a leading cause of global childhood mortality and morbidity. Serological evidence indicates that in the western world approximately 95% of all children have been infected with RSV by the age of two and 100% of children have been exposed by the time they reach adulthood.

RSV is a seasonal infectious disease that generally runs from November to March/April in the Northern Hemisphere. In more tropical climates, the annual epidemics are more variable, often coinciding with the wet season. In most cases the RSV infections will only cause minor upper respiratory illness with symptoms resembling that of the common cold. However, severe infection with the virus may result in bronchiolitis or pneumonia which may result in hospitalization or death. Further, since the immune response to RSV infection is not protective, RSV infections reoccur throughout adulthood. Annual re-infection rates in adults of 3-6% have been observed.

RSV is the predominant cause of acute LRTI in infants. Symptoms of RSV infection include bronchiolitis, cough, wheezing, rales (crackling in the lungs), low grade fever (38.3° C.), decreased oral intake and in more advanced cases of infection cyanosis can occur with up to 20% of patients developing an elevated temperature. In a given year, it is estimated that in the United States alone, 4-5 million children under the age of 4 years will develop an acute RSV infection and more than 125,000 infants are hospitalized with an RSV related illness. Between 25-40% of infants with RSV infections will show signs of pneumonia and bronchiolitis. The risk and severity of RSV infections is increased in infants with, for example, chronic co-existing medical conditions such as chronic lung disease, congenital heart disease, those who have been born prematurely and those with immunodeficiency.

In adults and older children, RSV infection has been associated with upper respiratory infection, tracheobronchitis, and otitis media. However, RSV in the institutionalized elderly can be more serious and is characterized by severe pneumonia and mortality rates of up to 20 and 78%, respectively. Adults with a previous history of heart conditions, such as congestive heart failure, or lung conditions, such as chronic obstructive pulmonary disease (COPD), pneumonia and asthma are at a high risk for RSV infection as are immunocompromised adults, for example those receiving haematopoietic stem cell or lung transplants and leukemia patients.

RSV infections place a significant burden on the healthcare system. This is particularly so in the case of infants such as, for example, immunodeficient infants which on average spend twice as long in hospital as other patients with an RSV infection (7-8 days compared to 3-4 days). Hospitalisation of infants with acute RSV-related bronchiolitis or RSV-related pneumonia involves supportive care management with oxygen therapy, fluids to prevent dehydration, nasal suctioning and respiratory support. There is also an economic impact associated with parents taking time away from work to care for their child.

RSV is a member of the order Mononegavirales, which consists of the non-segmented negative strand RNA viruses in the Families Paramyxoviridae, Rhabdoviridae and Filoviridae. RSV of humans (often also termed RSV or HRSV) is a member of the *Pneumovirus* genus of the sub-family Pneumovirinae within the Family Paramyxoviridae. Based on genetic and antigenic variations in the structural proteins, RSV is classified into two subgroups, A and B (Mufson, M. et al., J. Gen. Virol. 66:2111-2124). Other members of the *Pneumovirus* genus include viruses such as bovine RSV (BRSV), ovine RSV (ORSV) and pneumonia virus of mice (PVM) amongst others.

In addition to the genome features described above, family characteristics include a lipid envelope containing one or more glycoprotein species considered to be associated with attachment and entry of the host cell. Entry is considered to require a process by which the viral envelope fuses with the membrane of the host cell. Fusion of infected cells with, for example, their neighbours, can also result in the formation of fused multinucleate cells known as syncytia in some cases. The fusion process is believed to be glycoprotein mediated and is a feature shared with diverse enveloped viruses in other taxonomic groups. In the case of the Paramyxoviridae viruses of all genera characteristically express a fusion glycoprotein (F) which mediates membrane fusion.

The only small molecule drug currently approved for the treatment of severe RSV is the antiviral medication, Virazole® (ribavirin solution for inhalation). This agent has a broad spectrum antiviral with virustatic effects, and acts by inhibiting RSV replication. Unfortunately, due to its toxicity, administration of the agent is confined to a hospital setting. Its administration is further complicated by the need to follow a strict procedural process when administering the agent in order to minimise the likelihood of certain adverse affects. The agent has a number of adverse effects including sudden deterioration of respiratory function (bronchiospasm). Virazole is rarely prescribed due to its cost and potential toxicity. The efficacy of Virazole has remained controversial.

In the absence of an effective RSV antiviral therapy a number of preventative strategies have been investigated. There are no vaccines licensed for RSV but some success has been achieved in the area of prevention for infants at high risk of serious lower respiratory tract disease caused by RSV, as well as a reduction of LRTIs. One immunoglobulin-based therapy approved to protect high-risk infants from serious LRTIs is RSV-IGIV (RSV-immunoglobulin intravenous, also known as RespiGam™). RespiGam was licensed by the Food and Drug Administration in January 1996 for prevention of severe RSV lower respiratory tract disease in infants and children younger than 24 months with chronic lung disease (CLD) or a history of preterm birth (≤35 weeks' gestation).

Synagis® (palivizumab) is another immunoglobulin-based therapy, more specifically, a monoclonal antibody which is indicated for the preventing RSV-related serious lower tract disease in high risk paediatric patients. In June 1998, the Food and Drug Administration approved Synagis for administration as a monthly intramuscular injection commencing before the onset of the RSV season and continuing for a total of five doses. However difficulties with administration and its high cost is prohibitive to widespread use. Further, the American Association of Paediatricians (AAP) recently updated its recommendations for use of Synagis the effect of which further restricts the use to infants at the highest risk of hospitalisation during times according to likely RSV circulation. Approximately 70% of the infant population hospitalised with severe RSV disease are term infants, which in the absence of approval to treat, are not candidates for receiving Synagis.

Accordingly, there remains an ongoing need for new compounds that are useful in the treatment of RSV infections.

WO2008/037011 describes compounds that are useful in the treatment of RSV infections. The compounds of the present invention fall within the generic scope of WO2008/037011, but are not specifically disclosed therein. The inventors of the present invention have discovered a novel class of compounds which possess properties considered to be desirable in a drug-like compound suitable for the treatment of RSV infections in humans. Desirable properties include potency against RSV; enhanced aqueous solubility; good stability in media such as aqueous solutions, blood and plasma; low or intermediate binding to human plasma proteins and low inhibition of the hERG ion channel (e.g. hERG $IC_{50}$>500 times higher than RSV $EC_{50}$).

SUMMARY

According to a first aspect there is provided a compound of formula (I), racemates, isomers and/or salts thereof:

(I)

wherein $X_1$ and $X_2$ are independently selected from CH and N wherein at least one of $X_1$ or $X_2$ is N;

$R_1$ is optionally substituted and is selected from a carbocyclic, heterocyclic and aromatic ring;

$R_2$ is selected from $C_{1-6}$alkyl, halo$C_{1-3}$alkyl and $C_{1-3}$alkoxy; and $R_3$ is H or an optional substituent.

In a preferred embodiment, $R_2$ is $C_{1-3}$alkyl or $CF_3$ with methyl being particularly preferred.

In yet another preferred embodiment $X_1$ is N. In a particularly preferred embodiment $X_1$ is N and $X_2$ is CH. In another particularly preferred embodiment $X_1$ is N and $X_2$ is N.

In still another preferred embodiment $R_3$ is H.

In a second aspect, there is provided a process for preparing the compounds of formula (I), racemates, isomers and/or salts thereof comprising the step of reacting a compound of formula II:

(II)

with a compound of formula III:

(III)

under acylation conditions;

wherein $X_1$, $X_2$, $R_1$, $R_2$ and $R_3$ are as defined in formula (I).

The compounds of formula (I) are RSV antiviral agents and are useful in the treatment of RSV infections. Accordingly, the compounds of the invention are therefore also useful in the treatment of RSV diseases, such as bronchiolitis or pneumonia, or in reducing exacerbation of underlying or pre-existing respiratory diseases or conditions wherein RSV infection is a cause of said exacerbation. The underlying or pre-existing respiratory diseases or conditions may include asthma, chronic obstructive pulmonary disease (COPD) and immunosuppression such as immunosuppression experienced by bone marrow transplant recipients.

In a third aspect there is provided an RSV antiviral agent comprising the compound of formula (I), racemates, isomers and/or salts thereof.

There is also provided use of the compound of formula (I), racemates, isomers and/or salts thereof as a RSV antiviral agent.

There is further provided the compound of formula (I), racemates, isomers and/or salts thereof for use as an RSV antiviral agent.

The compound of formula (I), racemates, isomers and/or salts thereof may also be administered in the form of a pharmaceutical composition together with a pharmaceutically acceptable carrier.

In a fourth aspect there is provided a pharmaceutical composition comprising the compound of formula (I), racemates, isomers and/or salts thereof and a pharmaceutically acceptable carrier.

In one embodiment, the antiviral agent or composition also comprises one or more other RSV antiviral agents.

In a fifth aspect there is provided a method of treating an RSV infection comprising the step of administering the compound of formula (I), racemates, isomers and/or salts thereof, antiviral agent or pharmaceutical composition thereof to a subject in need thereof.

In a sixth aspect there is provided a method of treating an RSV disease comprising the step of administering the compound of formula (I), racemates, isomers and/or salts thereof, antiviral agent or pharmaceutical composition thereof to a subject in need thereof. There is also provided a method of reducing exacerbation of an underlying or pre-existing respiratory disease wherein RSV infection is a cause of said exacerbation comprising the step of administering the compound of formula (I), racemates, isomers and/or salts thereof, antiviral agent or pharmaceutical composition thereof to a subject in need thereof.

There is further provided use of the compound of formula (I), racemates, isomers and/or salts thereof, antiviral agent or pharmaceutical composition thereof in the manufacture of a medicament for treating an RSV infection or an RSV disease or reducing exacerbation of an underlying or pre-existing respiratory disease wherein RSV infection is a cause of said exacerbation.

There is still further provided use of the compound of formula (I), racemates, isomers and/or salts thereof, antiviral agent or pharmaceutical composition thereof for treating an RSV infection or an RSV disease or reducing exacerbation of an underlying or pre-existing respiratory disease wherein RSV infection is a cause of said exacerbation.

There is even further provided the compound of formula (I), racemates, isomers and/or salts thereof, antiviral agent or pharmaceutical composition thereof for use in treating an RSV infection or RSV disease or reducing exacerbation of an underlying or pre-existing respiratory disease wherein RSV infection is a cause of said exacerbation.

DETAILED DESCRIPTION

The present invention relates to compounds of formula (I), racemates, isomers and/or salts thereof, which are RSV antiviral agents and are useful in treating RSV infections or an RSV disease or reducing exacerbation of an underlying or pre-existing respiratory disease wherein RSV infection is a cause of said exacerbation.

Without wishing to be bound by theory, it is believed that the combination of a 3-substituted isoxazol-4-yl and the heteroaromatic core ring provides a new class of potent RSV antivirals with desirable properties. The position of the nitrogen(s) in the fused heteroaromatic core ring is also believed to influence the compound properties.

Compounds

In one embodiment there is provided a compound of formula (I), racemates, isomers and/or salts thereof:

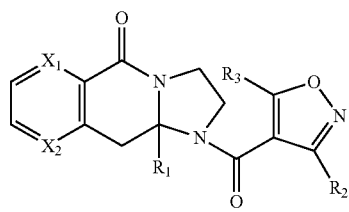

(I)

wherein $X_1$ and $X_2$ are independently selected from CH and N wherein at least one of $X_1$ or $X_2$ is N;

$R_1$ is optionally substituted and is selected from a 3-10 membered carbocyclic ring such as a 3-7 membered cycloalkyl or a 9-10 membered membered fused bicyclic carbocyclic ring; a 5-6 membered monocyclic heterocyclyl; a 9-10 membered fused bicyclic heterocyclyl; and a 6-membered aromatic ring;

$R_2$ is selected from $C_{1-3}$alkyl, halo$C_{1-3}$alkyl and $C_{1-3}$alkoxy; and $R_3$ is H or an optional substituent.

In a further embodiment there is provided a compound of formula (I), racemates, isomers and/or salts thereof, wherein $R_1$ is optionally substituted and is selected from a $C_6$cycloalkyl, phenyl, a 5-6 membered heterocyclyl and a 9-membered fused bicyclic heterocyclyl. 6-Membered rings such as $C_6$cycloalkyl, 6-membered heterocyclyl and phenyl are particularly preferred with aromatic rings such as phenyl and 6-membered heterocyclyl being even more preferred. Examples of $R_1$ include phenyl, piperidinyl, pyridinyl, pyridazinyl, pyrimidinyl, pyrazinyl, tetrahydropyranyl, cyclohexyl, cyclohexanone, cyclopentyl, benzimidazolyl, dihydrobenzofuryl, thianyl, thianyl oxide, thianyl dioxide, benzodiozolyl, indolyl, piperidinonyl and indolinyl. Phenyl is particularly preferred.

In one embodiment $R_1$ is substituted with one, two or three optional substituents. In a further embodiment, $R_1$ is disubstituted. In a particularly preferred embodiment, $R_1$ is monosubstituted.

In one embodiment, when $R_1$ is a 6-membered ring and is optionally monosubstituted or disubstituted, then $R_1$ may preferably be para and/or meta substituted, more preferably para substituted.

In still a further embodiment, when $R_1$ is an optionally substituted phenyl, $R_1$ may preferably be para and/or meta substituted, more preferably para substituted. In a particularly preferred embodiment $R_1$ is a para-substituted phenyl.

Particularly preferred substituents on $R_1$ include halogens such as F or Cl; $C_{1-4}$alkyl such as methyl; $C_{1-4}$alkoxy such as $OCH_3$ or $CH_2OCH_3$; OH; halo$C_{1-4}$alkyl such as $CF_3$ or $CHF_2$; $C_{1-4}$alkylOH such as $CH_2OH$, 5-6 membered heterocyclyl containing nitrogen and/or oxygen such as morpholinyl, piperizinyl or pyrrolidinyl; $N(C_{1-4}alkyl)_2$ such as $—N(CH_3)_2$; $—O—(CH_2)_{1-4}OH$ such as $—OCH_2CH_2OH$; and $—O—(CH_2)_{1-4}OC_{1-4}alkyl$ such as $—OCH_2CH_2OCH_3$. Even more preferred substituents on $R_1$ include $C_{1-3}$alkyl, $C_{1-3}$alkoxy, halo$C_{1-3}$alkyl and halo with methyl, methoxy, $CF_3$, Cl and F being particularly preferred and Cl and F being most preferred.

In another embodiment, there is provided a compound of formula (Ia), racemates, isomers and/or salts thereof:

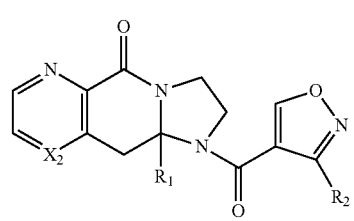

(Ia)

wherein $X_2$, $R_1$ and $R_2$ are as defined for formula (I).

In another embodiment, there is provided a compound of formula (Ib), racemates, isomers and/or salts thereof:

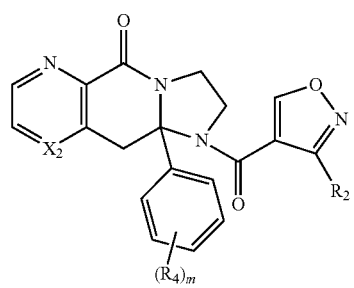

(Ib)

wherein $X_2$ and $R_2$ are as defined for formula (I), m is an integer selected from 0, 1, 2 or 3, and $R_4$ is an optional substituent. In one embodiment of formula (Ib), $X_2$ is CH. In yet another embodiment of formula (Ib), $X_2$ is N.

Preferably m is 1 or 2, more preferably 1, and the optional substituents are as previously defined for $R_1$. $C_{1-3}$alkyl, halo$C_{1-3}$alkyl, halo or $C_{1-3}$alkoxy are particularly preferred $R_4$ groups, with methyl, methoxy, $CF_3$ and halo being even more preferred and Cl and F being most preferred.

In a particularly preferred embodiment, there is provided a compound of formula (Ic), racemates, isomers and/or salts thereof:

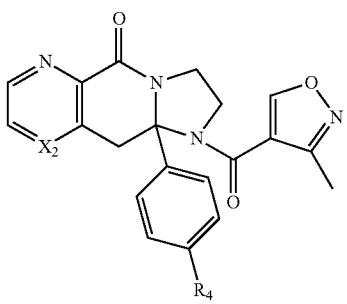

(Ic)

wherein $X_2$ is as defined for formula (I) and $R_4$ is an optional substituent as previously defined. In one embodiment of formula (Ic), $X_2$ is CH and $R_4$ is selected from $C_{1-3}$alkyl, halo$C_{1-3}$alkyl, halo or $C_{1-3}$alkoxy, more preferably methyl, methoxy, $CF_3$ and halo with Cl and F being particularly preferred. In yet another embodiment of formula (Ic), $X_2$ is N and $R_4$ is selected from $C_{1-3}$alkyl, halo$C_{1-3}$alkyl, halo or $C_{1-3}$alkoxy, more preferably methyl, methoxy, $CF_3$ and halo with Cl and F being particularly preferred.

In another embodiment there is provided a compound or its racemates, single enantiomers, mixtures of enantiomers in any ratio and/or salts thereof selected from the group consisting of:

(1) 5a-(4-chlorophenyl)-6-[(3-methyl-1,2-oxazol-4-yl)carbonyl]-5a,6,7,8-tetrahydroimidazo[1',2':1,6]pyrido[3,4-b]pyrazin-10(5H)-one;
(2) 10a-(4-chlorophenyl)-1-[(3-methyl-1,2-oxazol-4-yl)carbonyl]-2,3,10,10a-tetrahydroimidazo[2,1-g][1,7]naphthyridin-5(1H)-one;
(3) 10a-(4-methoxyphenyl)-1-[(3-methyl-1,2-oxazol-4-yl)carbonyl]-2,3,10,10a-tetrahydroimidazo[2,1-g][1,7]naphthyridin-5(1H)-one;
(4) 10a-(4-fluorophenyl)-1-[(3-methyl-1,2-oxazol-4-yl)carbonyl]-2,3,10,10a-tetrahydroimidazo[2,1-g][1,7]naphthyridin-5(1H)-one;
(5) 5a-(4-fluorophenyl)-6-[(3-methyl-1,2-oxazol-4-yl)carbonyl]-5a,6,7,8-tetrahydroimidazo[1',2':1,6]pyrido[3,4-b]pyrazin-10(5H)-one;
(6) 10a-(4-fluoro-3-methylphenyl)-1-[(3-methyl-1,2-oxazol-4-yl)carbonyl]-2,3,10,10a-tetrahydroimidazo[2,1-g][1,7]naphthyridin-5(1H)-one;
(7) 10a-(3,4-difluorophenyl)-1-[(3-methyl-1,2-oxazol-4-yl)carbonyl]-2,3,10,10a-tetrahydroimidazo[2,1-g][1,7]naphthyridin-5(1H)-one;
(8) 5a-(3,4-difluorophenyl)-6-[(3-methyl-1,2-oxazol-4-yl)carbonyl]-5a,6,7,8-tetrahydroimidazo[1',2':1,6]pyrido[3,4-b]pyrazin-10(5H)-one;
(9) 5a-(4-fluoro-3-methylphenyl)-6-[(3-methyl-1,2-oxazol-4-yl)carbonyl]-5a,6,7,8-tetrahydroimidazo[1',2':1,6]pyrido[3,4-b]pyrazin-10(5H)-one;
(10) 10a-(2-chlorophenyl)-1-[(3-methyl-1,2-oxazol-4-yl)carbonyl]-2,3,10,10a-tetrahydroimidazo[2,1-g][1,7]naphthyridin-5(1H)-one;
(11) 10a-cyclohexyl-1-[(3-methyl-1,2-oxazol-4-yl)carbonyl]-2,3,10,10a-tetrahydroimidazo[2,1-g][1,7]naphthyridin-5(1H)-one;
(12) 10a-(4,4-difluorocyclohexyl)-1-[(3-methyl-1,2-oxazol-4-yl)carbonyl]-2,3,10,10a-tetrahydroimidazo[2,1-g][1,7]naphthyridin-5(1H)-one;
(13) 10a-(4-chlorophenyl)-1-{[3-(trifluoromethyl)-1,2-oxazol-4-yl]carbonyl}-2,3,10,10a-tetrahydroimidazo[2,1-g][1,7]naphthyridin-5(1H)-one; and
(14) 10a-(2,3-dihydro-1-benzofuran-5-yl)-1-[(3-methyl-1,2-oxazol-4-yl)carbonyl]-2,3,10,10a-tetrahydroimidazo[2,1-g][1,7]naphthyridin-5(1H)-one.

The person skilled in the art will understand that a compound possessing a chiral centre may exist as a racemate, a single enantiomer or a mixture of enantiomers in any ratio thereof.

Accordingly, in yet another embodiment there is provided a compound of formula (I) (or its salts thereof) as a single enantiomer or a mixture of enantiomers in any ratio thereof. More preferably the compound of formula (I) is in the form of a single enantiomer of formula (I-i) or its salts thereof:

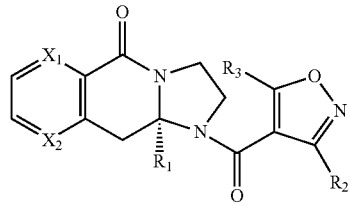

(I-i)

wherein $X_1$, $X_2$, $R_1$, $R_2$ and $R_3$ are as defined for formula (I).

In a further embodiment there is provided a compound of formula (Ia-i) or its salts thereof:

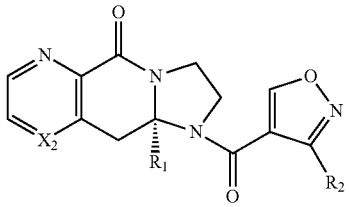

(Ia-i)

wherein $X_2$, $R_1$ and $R_2$ are as defined for formula (I).

In still a further embodiment there is provided a compound of formula (Ib-i) or its salts thereof:

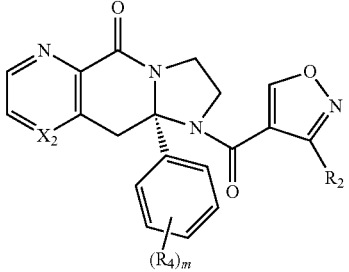

(Ib-i)

wherein $X_2$ and $R_2$ are as defined for formula (I) and m and $R_4$ are as defined for formula (Ib). $C_{1-3}$alkyl, halo$C_{1-3}$alkyl, halo or $C_{1-3}$alkoxy are particularly preferred $R_4$ groups, with methyl, methoxy, $CF_3$ and halo being even more preferred and Cl and F being most preferred. In one embodiment of formula (Ib-i), $X_2$ is CH. In yet another embodiment of formula (Ib-i), $X_2$ is N.

In yet another further embodiment there is provided a compound of formula (Ic-i) or its salts thereof:

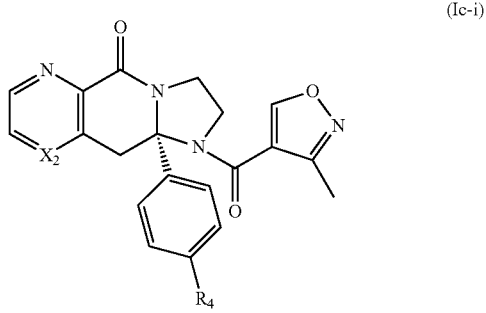

(Ic-i)

wherein $X_2$ is as defined for formula (I) and $R_4$ is an optional substituent as previously defined. In one embodiment of formula (Ic-i), $X_2$ is CH and $R_4$ is selected from $C_{1-3}$alkyl, halo$C_{1-3}$alkyl, halo or $C_{1-3}$alkoxy, more preferably methyl, methoxy, $CF_3$ and halo with Cl and F being particularly preferred. In yet another embodiment of formula (Ic-i), $X_2$ is N and $R_4$ is selected from $C_{1-3}$alkyl, halo$C_{1-3}$alkyl, halo or $C_{1-3}$alkoxy, more preferably methyl, methoxy, $CF_3$ and halo with Cl and F being particularly preferred.

In still another embodiment there is provided a compound of formula (I) in the form of a single enantiomer or its salts thereof selected from the group consisting of:
(1A) (5aS)-5a-(4-chlorophenyl)-6-[(3-methyl-1,2-oxazol-4-yl)carbonyl]-5a,6,7,8-tetrahydroimidazo[1',2':1,6]pyrido[3,4-b]pyrazin-10(5H)-one;
(2A) (10aS)-10a-(4-chlorophenyl)-1-[(3-methyl-1,2-oxazol-4-yl)carbonyl]-2,3,10,10a-tetrahydroimidazo[2,1-g][1,7]naphthyridin-5(1H)-one;
(4A) (10aS)-10a-(4-fluorophenyl)-1-[(3-methyl-1,2-oxazol-4-yl)carbonyl]-2,3,10,10a-tetrahydroimidazo[2,1-g][1,7]naphthyridin-5(1H)-one
(5A) (5aS)-5a-(4-fluorophenyl)-6-[(3-methyl-1,2-oxazol-4-yl)carbonyl]-5a,6,7,8-tetrahydroimidazo[1',2':1,6]pyrido[3,4-b]pyrazin-10(5H)-one; and
(6A) (10aS)-10a-(4-fluoro-3-methylphenyl)-1-[(3-methyl-1,2-oxazol-4-yl)carbonyl]-2,3,10,10a-tetrahydroimidazo[2,1-g][1,7]naphthyridin-5(1H)-one As used herein the term "isoxazole" means a 1,2-oxazole.

As used herein, the term "$C_{1-6}$alkyl" or "$C_{1-3}$alkyl" encompasses optionally substituted straight chain or branched chain hydrocarbon groups having from 1 to 6 or 1 to 3 carbon atoms and encompasses groups of the formula —$C_xH_{2x+1}$, where x is an integer of 1 to 6. Examples include methyl, ethyl, propyl, isopropyl, butyl, isobutyl, sec-butyl, tert-butyl, pentyl, neopentyl hexyl, and so forth. Unless the context requires otherwise, the term "$C_{1-6}$alkyl" also encompasses alkyl groups containing one less hydrogen atom such that the group is attached via two positions. Such groups are also referred to as "$C_{1-6}$alkylene" groups.

As used herein, the term "$C_{1-6}$alkoxy" or "$C_{1-4}$alkoxy" or "$C_{1-3}$alkoxy" refers to the group —$OC_xH_{2x+1}$, where x is an integer of 1 to 6, or of 1 to 4, or of 1 to 3. Examples include methoxy, ethoxy, propoxy, isoproxy, butoxy, tert-butoxy, pentoxy and so forth. The oxygen atom may be located along the hydrocarbon chain, and need not be the atom linking the group to the remainder of the compound.

As used herein, the term "halo$C_{1-6}$alkyl" or "halo $C_{1-4}$alkyl" or "halo$C_{1-3}$alkyl" refers to a $C_{1-6}$alkyl, or a $C_{1-4}$alkyl or a $C_{1-3}$alkyl which is substituted with one or more halogens, such as for example, $CHF_2$ and $CF_3$.

The term "$C_{2-6}$alkenyl" refers to optionally substituted straight chain or branched chain hydrocarbon groups having at least one double bond of either E or Z stereochemistry where applicable and 2 to 6 carbon atoms. Examples include vinyl, 1-propenyl, 1- and 2-butenyl, 2-methyl-2-propenyl hexenyl, butadienyl, hexadienyl, hexatrienyl and so forth. Unless the context requires otherwise, the term "$C_{1-6}$alkenyl" also encompasses alkenyl groups containing one less hydrogen atom such that the group is attached via two positions. Such groups are also referred to as "$C_{2-6}$alkenylene" groups.

The term "$C_{2-6}$alkynyl" refers to optionally substituted straight chain or branched chain hydrocarbon groups having at least one triple bond and 2 to 6 carbon atoms. Examples include ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl, 5-hexynyl and so forth. Unless the context indicates otherwise, the term "$C_{2-6}$alkynyl" also encompasses alkynyl groups containing one less hydrogen atom such that the group is attached via two positions. Such groups are also referred to as "$C_{2-6}$alkynylene" groups.

As used herein, the term "carbocyclic" encompasses cycloalkyl and fused cycloalkyl groups. Examples include 3-10 membered carbocyclic rings such as 3-8 membered cycloalkyl or 9-10 membered fused bicyclic carbocyclic rings.

The term "cycloalkyl" refers to non-aromatic cyclic hydrocarbon groups which may have from 3 to 8 carbon atoms, including cyclopropyl, cyclobutyl, cyclopentyl, cyclohexyl, cyclohexenyl, cycloheptyl, cyclooctyl and so forth. It will be understood that cycloalkyl groups may be saturated such as cyclohexyl or unsaturated such as cyclohexenyl. It will also be understood that cycloalkyl groups include cycloketones such as cyclopentanone, cyclohexanone or cycloheptanone.

The term "fused cycloalkyl" refers to two cycloalkyl groups which are fused together to form a 9-10 membered fused bicyclic carbocyclic ring. Examples include decalin and hexahydroindane.

The term "aromatic ring" or "aryl" refers to any group containing a carbocyclic (non-heterocyclic) aromatic ring or an aromatic heterocyclyl and may be a mono-, bi- or tri-cyclic ring system. The aromatic ring or ring system is generally composed of 6 to 10 carbon atoms. Such groups may contain fused ring systems (such as napthyl, tetrahydronapthyl, fluorenyl, indenyl, azulenyl, anthracenyl and the like), linked ring systems (such as biphenyl groups), and may be substituted or unsubstituted.

Examples of carbocyclic aromatic groups include aryl groups such as phenyl, biphenyl, naphthyl and tetrahydronaphthyl.

The term "heterocyclyl" or "heterocyclic" encompasses aromatic heterocyclyls and non-aromatic heterocyclyls.

The term "aromatic heterocyclyl" may be used interchangeably with the term "heteroaromatic" or the term "heteroaryl". The term "aromatic heterocyclyl" also encompasses pseudoaromatic heterocyclyls. The term "pseudoaromatic" refers to a ring system which is not strictly aromatic, but which is stabilized by means of delocalization of electrons and behaves in a similar manner to aromatic rings. The heteroatoms in the aromatic heterocyclyl group may be selected from N, S and O. Such groups may be substituted or unsubstituted.

Aromatic heterocyclyl groups may be 5 membered or 6 membered mono-cyclic aromatic ring systems, such as 5 membered aromatic heterocyclyls containing oxygen and/or nitrogen or 6 membered aromatic heterocyclyls containing 1 or 2 nitrogens.

Examples of 5 membered mono-cyclic aromatic ring systems include furanyl, thienyl, pyrrolyl, oxazolyl, oxadiazolyl (including 1,2,3 and 1,2,4 oxadiazolyls), thiazolyl, isoxazolyl, furazanyl, isothiazolyl, pyrazolyl, imidazolyl, triazolyl (including 1,2,3, 1,2,4 and 1,3,4 triazolyls), tetrazolyl, thiadiazolyl (including 1,2,3 and 1,3,4 thiadiazolyls) and so forth. Examples of 6 membered mono-cyclic aromatic ring systems include pyridinyl, pyrimidinyl, pyridazinyl, pyrazinyl, triazinyl and so forth. Examples of 6 membered aromatic heterocyclyls containing 1 nitrogen include pyridyl. Examples of 6 membered aromatic heterocyclyls containing 2 nitrogens include pyrazinyl.

Aromatic heterocyclyl groups may also be bicyclic or polycyclic heteroaromatic ring systems such as fused ring systems (including purine, pteridinyl, napthyridinyl, 1H thieno[2,3-c]pyrazolyl, thieno[2,3-b]furyl and the like) or linked ring systems (such as oligothiophene, polypyrrole and so forth). Fused ring systems may also include aromatic 5 membered or 6 membered heterocyclyls fused to carbocyclic aromatic rings such as phenyl, napthyl, indenyl, azulenyl, fluorenyl, anthracenyl and the like, such as 5 membered aromatic heterocyclyls containing nitrogen fused to phenyl rings, 5 membered aromatic heterocyclyls containing 1 or 2 nitrogens fused to phenyl ring Examples of aromatic heterocyclyls fused to carbocyclic aromatic rings include benzothiophenyl, indolyl, isoindolyl, benzofuranyl, isobenzofuranyl, benzimidazolyl, indazolyl, benzoxazolyl, benzisoxazolyl, benzothiazolyl, benzisothiazolyl, benzimidazolyl, indazolyl, quinolinyl, isoquinolinyl, quinoxalinyl, quinazolinyl, cinnolinyl, benzotriazinyl, phthalazinyl, carbolinyl and so forth. Examples of 5 membered aromatic heterocyclyls containing 1 nitrogen fused to a phenyl ring include indolyl. Examples of 5 membered aromatic heterocyclyls containing two nitrogens fused to a phenyl ring include benzimidazolyl.

It will be understood that suitable derivatives of aromatic heterocyclyls containing nitrogen include N-oxides thereof.

The term "non-aromatic heterocyclyl" encompasses optionally substituted saturated and unsaturated rings which contain at least one heteroatom selected from the group consisting of O, N and S. Non-aromatic heterocyclyls may be 5 membered, 6 membered or 7 membered mono-cyclic rings, such as 5 membered non-aromatic heterocyclyls containing nitrogen and/or oxygen, 5-membered non-aromatic heterocyclyls containing 1 nitrogen, 6 membered heterocyclyls containing oxygen, nitrogen and/or sulphur, 6 membered heterocyclyls containing 1 oxygen, sulfur or nitrogen, 6 membered heterocyclyls containing 2 nitrogens, and 6 membered heterocyclyls containing 1 nitrogen and 1 oxygen.

Examples of 5 membered non-aromatic heterocyclyl rings include 2H-pyrrolyl, 1-pyrrolinyl, 2-pyrrolinyl, 3-pyrrolinyl, pyrrolidinyl, 1-pyrrolidinyl, 2-pyrrolidinyl, 3-pyrrolidinyl, tetrahydrofuranyl, tetrahydrothiophenyl, pyrazolinyl, 2-pyrazolinyl, 3-pyrazolinyl, pyrazolidinyl, 2-pyrazolidinyl, 3-pyrazolidinyl, imidazolinyl, 3-dioxalanyl, thiazolidinyl, isoxazolidinyl, 2-imidazolinyl and the like. Examples of 5-membered non-aromatic heterocyclyls containing 1 nitrogen include pyrrolidinyl.

Examples of 6 membered non-aromatic heterocyclyls include piperidinyl, piperidinonyl, pyranyl, dihyrdopyranyl, tetrahydropyranyl, 2H pyranyl, 4H pyranyl, thianyl, thianyl oxide, thianyl dioxide, piperazinyl, diozanyl, 1,4-dioxinyl, 1,4-dithianyl, 1,3,5-triozalanyl, 1,3,5-trithianyl, 1,4-morpholinyl, thiomorpholinyl, 1,4-oxathianyl, triazinyl, 1,4-thiazinyl and the like. Examples of 6 membered heterocyclyls containing 1 oxygen include tetrahydropyranyl. Examples of 6 membered heterocyclyls containing 1 sulfur include thianyl, thianyl oxide and thianyl dioxide. Examples of 6 membered heterocyclyls containing 1 nitrogen include piperidinyl and piperidinonyl. Examples of 6 membered heterocyclyls containing 2 nitrogens include piperazinyl. Examples of 6 membered heterocyclyls containing 1 nitrogen and 1 oxygen include morpholinyl.

Examples of 7 membered non-aromatic heterocyclyls include azepanyl, oxepanyl, thiepanyl and the like.

Non-aromatic heterocyclyl rings may also be bicyclic heterocyclyl rings such as linked ring systems (for example uridinyl and so forth) or fused ring systems. Fused ring systems include non-aromatic 5 membered, 6 membered or 7 membered heterocyclyls fused to carbocyclic aromatic rings such as phenyl, napthyl, indenyl, azulenyl, fluorenyl, anthracenyl and the like, such as 5 membered non-aromatic heterocyclyls containing oxygen and/or nitrogen fused to phenyl rings, 5 membered non-aromatic heterocyclyls containing one oxygen or nitrogen fused to phenyl rings and 5 membered non-aromatic heterocyclyls containing two oxygens.

Examples of non-aromatic 5 membered, 6 membered or 7 membered heterocyclyls fused to carbocyclic aromatic rings include indolinyl, benzodiazepinyl, benzazepinyl, dihydrobenzofuranyl, benzodioxolyl and the like. Examples of 5 membered non-aromatic heterocyclyls containing one oxygen or nitrogen fused to phenyl rings include dihydrobenzofuranyl and indolinyl. Examples of 5 membered non-aromatic heterocyclyls containing two oxygens fused to phenyl rings include benzodioxolyl.

Unless otherwise defined, the term "optionally substituted" or "optional substituent" as used herein refers to a group which may or may not be further substituted with one or more groups selected from $C_{1-6}$alkyl, $C_{1-6}$alkenyl, $C_{1-6}$alkynyl, aryl, aldehyde, halogen, halo$C_{1-6}$alkyl, halo$C_{1-6}$alkenyl, halo$C_{1-6}$alkynyl, haloaryl, hydroxy, $C_{1-6}$alkylhydroxy, $C_{1-6}$alkoxy, —O$C_{1-6}$alkylhydroxy, —O$C_{1-6}$alkyl$C_{1-6}$alkoxy, $C_{1-6}$alkenyloxy, aryloxy, benzyloxy, halo$C_{1-6}$alkoxy, halo$C_{1-6}$alkenyloxy, haloaryloxy, nitro, nitro$C_{1-6}$alkyl, nitro$C_{1-6}$alkenyl, nitro$C_{1-6}$alkynyl, nitroaryl, nitroheterocyclyl, amino, $C_{1-6}$alkylamino, $C_{1-6}$dialkylamino, $C_{1-6}$alkenylamino, $C_{1-6}$alkynylamino, arylamino, diarylamino, benzylamino, dibenzylamino, acyl, $C_{1-6}$alkenylacyl, $C_{1-6}$alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphenyl, arylsulphenyl, carboalkoxy, carboaryloxy, mercapto, $C_{1-6}$alkylthio, benzylthio, acylthio, phosphorus-containing groups and the like.

The compounds of the invention may also be prepared as salts which are pharmaceutically acceptable. It will be appreciated that non-pharmaceutically acceptable salts also fall within the scope of the present invention, since these are useful as intermediates in the preparation of pharmaceutically acceptable salts. Examples of pharmaceutically acceptable salts include salts of pharmaceutically acceptable cations such as sodium, potassium, lithium, calcium, magnesium, ammonium, alkylammonium and the like; acid addition salts of pharmaceutically acceptable inorganic acids such as hydrochloric, orthophosphoric, sulfuric, phosphoric, nitric, carbonic, boric, sulfamic, hydrobromic acids and the like; and salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulfonic, trihalomethanesulfonic, toluenesulfonic, benzenesulfonic, isethionic, salicylic, sulphanilic, aspartic, glutamic, edetic, stearic, palmitic, oleic, lauric, pantothenic, tannic, ascorbic, valeric, orotic acids and the like. Salts of amine groups may also comprise quaternary ammonium salts in which the amino nitrogen atom carries a suitable organic group such as an alkyl, alkenyl, alkynyl, aralkyl moiety and so forth.

The salts may be formed by conventional means, such as by reacting the free base form of the compound with one or more equivalents of the appropriate acid.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, alcohols such as methanol, ethanol or isopropyl alcohol, DMSO, acetonitrile, dimethyl formamide (DMF) and the like with the solvate forming part of the crystal lattice by either non-covalent binding or by occupying a hole in the crystal lattice. Hydrates are formed when the solvent is water; alcoholates are formed when the solvent is alcohol. Solvates of the compounds of the present invention can be conveniently prepared or formed during the processes described herein.

It will be understood that compounds of formula (I) possess a chiral centre and may therefore exist as a racemate or an R- or S-enantiomer. The compounds may therefore be used as a purified enantiomer or diastereomer, or as a mixture of any ratio thereof. In one embodiment there is provided a compound of formula (I) as defined above in a single stereoisomeric form. The isomers may be separated conventionally by chromatographic methods or using a resolving agent. Alternatively the individual isomers may be prepared by asymmetric synthesis using chiral intermediates. Where the compound has at least one carbon-carbon double bond, it may occur in Z- and E-forms and all isomeric forms of the compounds being included in the present invention.

This invention also encompasses prodrugs of the compounds of formula (I).

The term "prodrug" is used herein in its broadest sense to include those compounds which are converted in vivo to the compound of formula (I). Use of the prodrug strategy optimises the delivery of the drug to its site of action. Compounds having free amino, amido, hydroxyl, or carboxylic acid groups may be converted into prodrugs.

Pharmaceutical Compositions

The invention also provides a pharmaceutical composition comprising a compound of formula (I), racemates, isomers and/or its pharmaceutically acceptable salts thereof and a pharmaceutically acceptable carrier.

The pharmaceutical composition may further comprise or be administered in combination with one or more other RSV antiviral agents such as Virazole®.

The term "composition" is intended to include the formulation of an active ingredient with conventional carriers and excipients, and also with encapsulating materials as the carrier, to give a capsule in which the active ingredient (with or without other carriers) is surrounded by the encapsulation carrier. Any carrier must be "pharmaceutically acceptable" meaning that it is compatible with the other ingredients of the composition and is not deleterious to a subject. The compositions of the present invention may contain other therapeutic agents as described above, and may be formulated, for example, by employing conventional solid or liquid vehicles or diluents, as well as pharmaceutical additives of a type appropriate to the mode of desired administration (for example, excipients, binders, preservatives, stabilizers, flavours and so forth) according to techniques such as those well known in the art of pharmaceutical formulation (See, for example, Remington: *The Science and Practice of Pharmacy*, 21st Ed., 2005, Lippincott Williams & Wilkins).

The pharmaceutical composition includes those suitable for oral, rectal, nasal, topical (including buccal and sub-lingual), vaginal or parenteral (including intramuscular, subcutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use.

Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

For preparing pharmaceutical compositions from the compounds of the present invention, pharmaceutically acceptable carriers can be either solid or liquid. Solid form preparations include powders, tablets, pills, capsules, cachets, suppositories, and dispensable granules. A solid carrier can be one or more substances which may also act as diluents, flavouring agents, solubilisers, lubricants, suspending agents, binders, preservatives, tablet disintegrating agents, or an encapsulating material.

Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with an encapsulating material as the carrier by providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

Liquid form preparations include solutions, suspensions, and emulsions, for example, water or water-propylene glycol solutions. For example, parenteral injection liquid preparations can be formulated as solutions in aqueous polyethylene glycol solution.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both.

The compositions according to the present invention may thus be formulated for parenteral administration (for example, by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilisation from solution, for constitution with a suitable vehicle, for example, sterile, pyrogen-free water, before use.

Pharmaceutical forms suitable for injectable use include sterile injectable solutions or dispersions, and sterile powders for the extemporaneous preparation of sterile injectable solutions. They should be stable under the conditions of manufacture and storage and may be preserved against oxidation and the contaminating action of microorganisms such as bacteria or fungi.

The solvent or dispersion medium for the injectable solution or dispersion may contain any of the conventional solvent or carrier systems for the compounds, and may contain, for example, water, ethanol, polyol (for example, glycerol, propylene glycol and liquid polyethylene glycol, and the like), suitable mixtures thereof, and vegetable oils.

Pharmaceutical forms suitable for injectable use may be delivered by any appropriate route including intravenous, intramuscular, intracerebral, intrathecal, epidural injection or infusion.

Sterile injectable solutions are prepared by incorporating the active compounds in the required amount in the appropriate solvent with various other ingredients such as these enumerated above, as required, followed by filtered sterilization. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, preferred methods of preparation are vacuum drying or freeze-drying of a previously sterile-filtered solution of the active ingredient plus any additional desired ingredients.

When the active ingredients are suitably protected they may be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like.

The amount of active compound in therapeutically useful compositions should be sufficient that a suitable dosage will be obtained.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin; or a flavouring agent such as peppermint, oil of wintergreen, or cherry flavouring. When the dosage unit form is a capsule, it may contain, in addition to materials of the above type, a liquid carrier.

Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations, including those that allow specific delivery of the compound(s) to specific regions of the gut.

Aqueous solutions suitable for oral use can be prepared by dissolving the active component in water and adding suitable colorants, flavours, stabilising and thickening agents, as desired. Aqueous suspensions suitable for oral use can be made by dispersing the finely divided active component in water with viscous material, such as natural or synthetic gums, resins, methylcellulose, sodium carboxymethylcellulose, or other well known suspending agents.

Pharmaceutically acceptable carriers and/or diluents include any and all solvents, dispersion media, coatings, antibacterial and antifungal agents, isotonic and absorption delaying agents and the like.

Also included are solid form preparations that are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilising agents, and the like.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension.

In the case of a spray, this may be achieved for example by means of a metering atomising spray pump. To improve nasal delivery and retention the compounds according to the invention may be encapsulated with cyclodextrins, or formulated with other agents expected to enhance delivery and retention in the nasal mucosa.

Administration to the respiratory tract may also be achieved by means of an aerosol formulation in which the active ingredient is provided in a pressurised pack with a suitable propellant such as a hydrofluorocarbon (HFC) for example hydrofluoroalkanes (HFA), carbon dioxide, or other suitable gas.

The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, for example gelatin, or blister packs from which the powder may be administered by means of an inhaler.

In formulations intended for administration to the respiratory tract, including intranasal formulations, the compound will generally have a small particle size for example of the order of 5 to 10 microns or less. Such a particle size may be obtained by means known in the art, for example by micronisation.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of viral infection in living subjects having a diseased condition in which bodily health is impaired as herein disclosed in detail.

The invention also includes the compounds in the absence of carrier where the compounds are in unit dosage form.

Liquids or powders for intranasal administration, tablets or capsules for oral administration and liquids for intravenous administration are the preferred compositions.

Methods of Treatment

The compounds of formula (I) have demonstrated sub-molar potency as inhibitors of RSV and therefore offer a method of treating an RSV infection. Accordingly, the compounds of formula (I) are considered to be useful to treat an RSV disease or reduce exacerbation of an underlying or pre-existing respiratory disease wherein RSV infection is a cause of said exacerbation. The RSV disease may include brochiolitis or pneumonia. The underlying or pre-existing respiratory diseases or conditions may include asthma, chronic obstructive pulmonary disease (COPD) and immunosuppression such as immunosuppression experienced by bone marrow transplant recipients.

Treatment may be therapeutic treatment or prophylactic treatment. Generally, the term "treating" means affecting a subject, tissue or cell to obtain a desired pharmacological and/or physiological effect and includes: (a) inhibiting the viral infection or RSV disease, such as by arresting its development or further development; (b) relieving or ameliorating the effects of the viral infection or RSV disease, such as by causing regression of the effects of the viral infection or RSV disease; (c) reducing the incidence of the viral infection or RSV disease or (d) preventing the infection or disease from occurring in a subject, tissue or cell predisposed to the viral infection or RSV disease or at risk thereof, but has not yet been diagnosed with a protective pharmacological and/or physiological effect so that the viral infection or RSV disease does not develop or occur in the subject, tissue or cell.

The term "subject" refers to any animal, in particular mammals such as humans, having a disease which requires treatment with the compound of formula (I). Particularly preferred treatment groups include at risk populations such as hospitalised subjects, the elderly, high-risk adults and infants.

The term "administering" should be understood to mean providing a compound or pharmaceutical composition of the invention to a subject suffering from or at risk of the disease or condition to be treated or prevented.

Although the invention has been described with reference to treating RSV infections or diseases, more particularly human and animal RSV infections or diseases, it will be appreciated that the invention may also be useful in the treatment of other viruses of the sub-family Pneumovirinae, more particularly, the genera *Pneumovirus* and *Metapneumovirus*.

Dosages

The term "therapeutically effective amount" refers to the amount of the compound of formula (I) that will elicit the biological or medical response of a subject, tissue or cell that is being sought by the researcher, veterinarian, medical doctor or other clinician.

In the prevention or treatment of RSV infections or diseases, an appropriate dosage level will generally be about 0.01 to about 500 mg per kg subject body weight per day which can be administered in single or multiple doses. The dosage may be selected, for example to any dose within any of these ranges, for therapeutic efficacy and/or symptomatic adjustment of the dosage to the subject to be treated.

It will be understood that the specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the subject undergoing therapy.

Methods

General Method A

Compounds of formula (I), racemates, isomers and/or salts thereof may be generally formed from reacting a precursor compound of formula II with a compound of formula III under acylation conditions wherein $X_1$, $X_2$, $R_1$, $R_2$ and $R_3$ are as defined in formula (I):

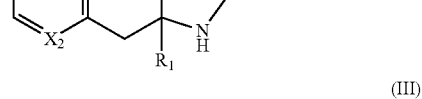

It will be generally understood that the racemate of a compound of formula (I) may be obtained, for example, by acylating the corresponding racemate of the precursor compound of formula (II). It will also be generally understood that isomers, for example stereoisomers, particularly enantiomers, of compounds of formula (I) may be obtained, for example, by acylating the corresponding isomer, stereoisomer or enantiomer, respectively, of the precursor compound of formula (II). Stereoisomers, particularly the enantiomers of compounds of formula (II) may be obtained by the methods described for their synthesis and/or separation which follow.

More particularly, compounds of the invention may be generally prepared using General Method A as follows (Scheme 1)

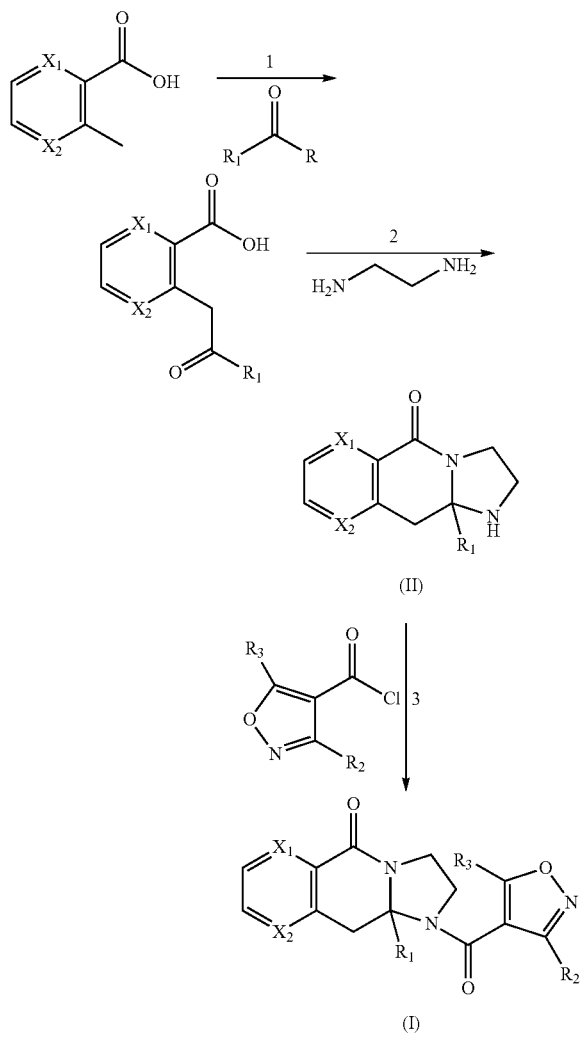

where R can be, but is not limited to, a leaving group such as O-alkyl, O-aryl, NCH$_3$OCH$_3$ and X$_1$, X$_2$, R$_1$, R$_2$ and R$_3$ are as previously defined.

Step 1:

In general, one equivalent of the appropriate acid, such as 3-methylpyridine-2-carboxylic acid, is treated with 3-4 equivalents of an appropriate base, such as LDA or KHMDS, in a suitable organic solvent such as THF at −78° C. The deprotonation is then stirred at −78° C. for at least 30 minutes, or at −78° C. for at least 30 minutes followed by −10 to 0° C. for at least 30 minutes. 1-1.2 equivalents of the appropriate electrophile are then added at −78° C. and the reaction allowed to proceed at −78° C. for at least 15 minutes. The reaction is either quenched at this temperature or allowed to warm to −10° C. to rt for at least 30 minutes. The reaction is quenched with water and washed with a suitable organic solvent, such as ethyl acetate, chloroform, or dichloromethane. The aqueous layer is then acidified with HCl (aq) and the resulting precipitated product collected by filtration and used as such in the next step. If no precipitate forms, the aqueous layer is extracted with a suitable organic solvent, such as ethyl acetate, chloroform, or dichloromethane. The organic layers are dried (MgSO$_4$ or Na$_2$SO$_4$) and concentrated in vacuo. The residue is used as such in the next step. Reference: J. Epsztajn et al. *Synth. Commun.* 1992, 22(9), 1239-1247.

Step 2:

In general, one equivalent of an appropriate keto-acid is reacted with 3-40 equivalents of ethylenediamine. The mixture is heated at reflux in an inert solvent, such as 1,2-dichloroethane or 1,4-dioxane, for 1-2 hours. After this time the reaction is allowed to cool before being concentrated in vacuo. The residue can be purified directly by flash chromatography, or suspended/dissolved in water and extracted with a suitable organic solvent such as dichloromethane. The organic layers are dried (MgSO$_4$ or Na$_2$SO$_4$) and concentrated in vacuo. The residue is then purified by flash chromatography.

Step 3:

In general, one equivalent of an appropriate cyclic amine in pyridine is added to 2.5-5 equivalents of an appropriate acid chloride in pyridine at 0° C. The acid chloride is initially prepared in situ by reacting the corresponding acid with thionyl chloride or with oxalyl chloride and catalytic DMF in dichloromethane. The acid chloride in some examples may be prepared in situ with cyanuric chloride and triethylamine in dichloromethane. The acylation reaction is allowed to warm to room temperature and monitored by LCMS. Once complete the reaction mixture is quenched with water or brine or sat. aq. NaHCO$_3$ and extracted with an organic solvent such as ethyl acetate or dichloromethane. The organic layers are dried (MgSO$_4$ or Na$_2$SO$_4$) and concentrated in vacuo. The residue is then purified by flash chromatography.

General Method for Separation of Stereoisomers

Compounds of the invention may be generally prepared as their single enantiomers by (a) separating their precursors i.e. of general formula (II) (which may be synthesised according to steps 1 and 2 of General Method A) into single enantiomers by HPLC using chromatographic columns with a chiral stationary phase such as Chiralpak IC 250×4.6 mm, Chiralpak AD-H 250×10 mm and Chiralpak AD-H 250×4.6 mm; followed by (b) acylation of the separated enantiomer with a compound of formula (III).

General Method for the Synthesis of Stereoisomers

Compounds of the invention may also be generally prepared as their single enantiomers by (a) forming a diastereomeric salt of a compound of formula (II) using an appropriate chiral acid; followed by (b) acylation of the separated enantiomer with a compound of formula (III).

EXAMPLES

Those skilled in the art will appreciate that the invention described herein is susceptible to variations and modifications other than those specifically described. The invention will now be described without limitation by reference to the examples which follow.

Compound Synthesis

¹H NMR spectra were recorded on either a Bruker Ultrashield™ 400 or AM 300 spectrometer. Spectra were recorded in CDCl₃, d₆-acetone, CD₃CN, CD₃OD or d₆-DMSO using the residual solvent peak as a reference. Chemical shifts are reported on the δ scale in parts per million (ppm) using the following conventions to assign the multiplicity: s (singlet), d (doublet), t (triplet), q (quartet) m (multiplet) and prefixed br (broad).

Mass spectra (ESI) were recorded on a Thermo Finnigan LCQ Advantage or LCQ Deca mass spectrometer coupled with a Thermo Finnigan Surveyor HPLC system. Unless stated otherwise, chromatography was performed with Phenomenex C8(2) or C18(2) columns. Water containing 0.1% formic acid (solvent A) and acetonitrile containing 0.1% formic acid (solvent B) were used for separations at acidic pH. Ammonium acetate (5 mM, solvent A) and methanol (solvent B) were used for separations at neutral pH.

Flash chromatography was performed on 40-63 μm silica gel 60 (Merck No. 9385) or using a Biotage SP4 (GraceResolv™ Silica Flash cartridges or C18 silica cartridges plugged in).

Example of General Method A 10a-(4-fluorophenyl)-1-[(3-methyl-1,2-oxazol-4-yl)carbonyl]-2,3,10,10a-tetrahydroimidazo[2,1-g][1,7]naphthyridin-5(1H)-one <<(4)>>

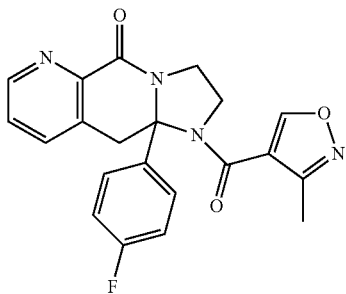 [SMILES: Cc1nocc1C(=O)N1CCN2C(=O)c3ncccc3CC12c1ccc(F)cc1]

Step 1:

To generate LDA: To a chilled (ice-acetone bath) solution of diisopropylamine (5.1 mL, 36 mmol) in dry THF (30 mL) was added n-BuLi (1.45 M solution in hexanes, 24 mL, 35 mmol) drop-wise and under an atmosphere of nitrogen. The solution was stirred for 15 minutes before being added to a suspension of 3-methylpyridine-2-carboxylic acid (1.5 g, 11 mmol) in THF (50 mL) drop-wise, at −78° C. and under an atmosphere of nitrogen. The dark purple mixture was stirred at −78° C. for 30 minutes and then at −5° C. for 30 minutes. After this time the mixture was re-cooled to −78° C. and a solution of methyl 4-fluorobenzoate (1.6 mL, 12 mmol) in THF (15 mL) was added. The dark brown mixture was stirred at −78° C. for 1.5 hours and then at 0° C. for 2.5 hours. The mixture was then poured into chilled water (50 mL) and washed with ethyl acetate (3×35 mL). The aqueous layer was acidified to pH 2 with HCl and extracted with ethyl acetate (3×75 mL). The three extracts were combined and concentrated in vacuo to yield 3-[2-(4-fluorophenyl)-2-oxoethyl]pyridine-2-carboxylic acid as a pale yellow solid (1.5 g, 53% yield). ESI-MI m/z [M+H]⁺ 259.95. ¹H NMR (400 MHz, DMSO) δ 8.61 (dd, J=4.7, 1.6 Hz, 1H), 8.14 (dd, J=8.9, 5.5 Hz, 2H), 7.86 (dd, J=7.8, 1.6 Hz, 1H), 7.62 (dd, J=7.7, 4.7 Hz, 1H), 7.40 (t, J=8.9 Hz, 2H), 4.78 (s, 2H).

Step 2:

To a suspension of 3-[2-(4-fluorophenyl)-2-oxoethyl]pyridine-2-carboxylic acid (1.5 g, 5.8 mmol) in 1,2-dichloroethane (100 mL) was added ethylenediamine (8 mL, 120 mmol) and the resulting solution heated at reflux for 1 hour. The resulting suspension was then allowed to cool to room temperature before being concentrated in vacuo to yield a thick, orange gum. The gum was suspended in methanol with the aid of sonication and filtered. The filtrate was adsorbed onto silica and purified by flash chromatography (5 to 7.5% methanol-dichloromethane) to yield 10a-(4-fluorophenyl)-2,3,10,10a-tetrahydroimidazo[2,1-g][1,7]naphthyridin-5(1H)-one as a pale yellow solid (1.1 g, 67% yield). ESI-MI m/z [M+H]⁺ 284.04. ¹H NMR (400 MHz, CDCl₃) δ 8.66 (brd, J=4.7 Hz, 1H), 7.36 (brd, J=7.7 Hz, 1H), 7.30 (dd, J=8.9, 5.2 Hz, 2H), 7.23 (dd, J=7.7, 4.7 Hz, 1H), 6.89 (t, J=8.7 Hz, 2H), 4.02-3.89 (m, 1H), 3.70-3.60 (m, 1H), 3.47 (d, J=15.2 Hz, 1H), 3.42 (d, J=15.2 Hz, 1H), 3.35 (ddd, J=12.4, 7.9, 2.8 Hz, 1H), 2.86-2.74 (m, 1H), 2.49 (brs, 1H).

Step 3:

To generate the acid chloride: To a chilled (ice bath) suspension of 3-methylisoxazole-4-carboxylic acid (110 mg, 0.87 mmol) in dichloromethane (1.5 mL) was added oxalyl chloride (0.3 mL) followed by DMF (1 drop, catalytic) under an atmosphere of nitrogen. The mixture was stirred at 0° C. for 10 minutes and then at room temperature for 1 hour. The resulting solution was concentrated under a stream of nitrogen to yield an oil. The oil was taken up in dichloromethane and re-concentrated to yield the acid chloride as a yellow oil which formed a thick suspension upon addition of pyridine.

To a chilled (ice bath) suspension of the acid chloride (generated as above, 0.87 mmol) in pyridine (0.8 mL) was added a suspension of 10a-(4-fluorophenyl)-2,3,10,10a-tetrahydroimidazo[2,1-g][1,7]naphthyridin-5(1H)-one (50 mg, 0.18 mmol) in pyridine (1.0 mL). The mixture was allowed to gradually warm to room temperature. After 4 hours, LCMS indicated complete reaction so the mixture was poured into water (4 mL) and extracted with ethyl acetate (3×6 mL). The extracts were combined, dried (MgSO₄), filtered and the filtrate concentrated in vacuo to yield a pale yellow oil. The material was purified by flash chromatography (80% acetone-hexanes to acetone) to yield the desired product (4) as an off-white solid after freeze-drying (59 mg, 84% yield). ESI-MI m/z [M+H]⁺ 392.99. ¹H NMR (400 MHz, CDCl₃) δ 8.66 (d, J=4.3 Hz, 1H), 8.52 (s, 1H), 7.59 (d, J=7.7 Hz, 1H), 7.50 (dd, J=9.0, 5.1 Hz, 2H), 7.33 (dd, J=7.7, 4.7 Hz, 1H), 6.98-6.86 (m, 2H), 4.75 (d, J=16.1 Hz, 1H), 4.48 (ddd, J=12.0, 8.7, 5.7 Hz, 1H), 4.06 (ddd, J=9.4, 8.7, 5.8 Hz, 1H), 3.97 (ddd, J=12.0, 8.3, 5.8 Hz, 1H), 3.87-3.73 (m, 2H), 2.42 (s, 3H).

The following compounds were similarly prepared using General Method A:

| Cpd. No. | Structure | ESI-MI m/z [M + H]+/1H-NMR |
|---|---|---|
| 1 | 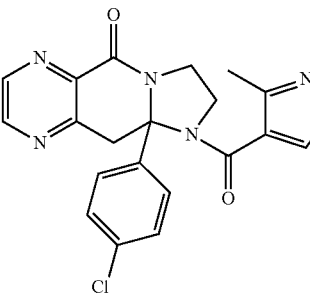 | ESI-MI m/z [M + H]+ 410.01. 1H NMR (400 MHz, CDCl3) δ 8.63 (d, J = 2.1 Hz, 1H), 8.60 (d, J = 2.4 Hz, 1H), 8.51 (s, 1H), 7.43 (d, J = 8.7 Hz, 2H), 7.24 (d, J = 8.7 Hz, 2H), 5.04 (d, J = 16.7 Hz, 1H), 4.56-4.41 (m, 1H), 4.19-3.96 (m, 2H), 3.92 (d, J = 16.9 Hz, 1H), 3.90-3.83 (m, 1H), 2.41 (s, 3H). |
| 2 | 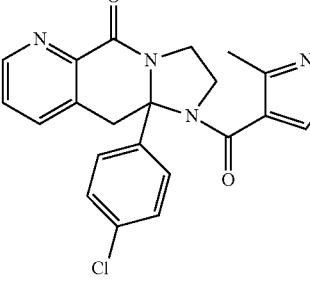 | ESI-MI m/z [M + H]+ 409.03. 1H NMR (400 MHz, CDCl3) δ 8.70-8.62 (m, 1H), 8.53 (s, 1H), 7.63-7.55 (m, 1H), 7.43 (d, J = 8.9 Hz, 2H), 7.34 (dd, J = 7.7, 4.7 Hz, 1H), 7.22 (d, J = 8.9 Hz, 2H), 4.74 (d, J = 16.1 Hz, 1H), 4.47 (ddd, J = 12.0, 8.7, 5.6 Hz, 1H), 4.06 (ddd, J = 9.5, 8.8, 5.8 Hz, 1H), 3.96 (ddd, J = 12.0, 8.3, 5.8 Hz, 1H), 3.85-3.71 (m, 2H), 2.42 (s, 3H). |
| 3 | 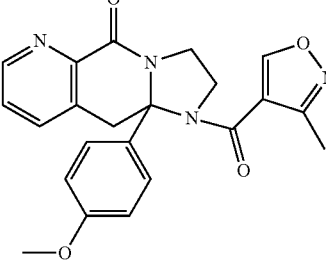 | ESI-MI m/z [M + H]+ 405.1. 1H NMR (400 MHz, Acetone) δ 9.07 (s, 1H), 8.53 (ddd, J = 4.6, 1.5, 1.1 Hz, 1H), 7.93-7.81 (m, 1H), 7.48-7.38 (m, 3H), 6.78 (d, J = 9.0 Hz, 2H), 4.78 (d, J = 16.1 Hz, 1H), 4.36 (ddd, J = 11.6, 8.9, 5.0 Hz, 1H), 4.24 (ddd, J = 10.0, 8.7, 6.3 Hz, 1H), 4.05 (ddd, J = 10.0, 8.4, 4.9 Hz, 1H), 3.92 (ddd, J = 11.7, 8.5, 6.5 Hz, 1H), 3.80 (d, J = 16.0 Hz, 1H), 3.71 (s, 3H), 2.34 (s, 3H). |
| 5 | 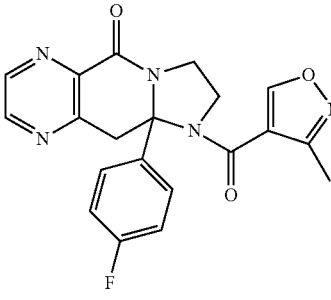 | ESI-MI m/z [M + H]+ 393.97. 1H NMR (400 MHz, CD3CN) δ 8.76 (s, 1H), 8.62 (d, J = 2.4 Hz, 1H), 8.61-8.57 (m, 1H), 7.46 (dd, J = 9.1, 5.2 Hz, 2H), 6.99 (t, J = 8.9 Hz, 2H), 4.81 (d, J = 16.6 Hz, 1H), 4.35 (ddd, J = 11.5, 8.3, 3.1 Hz, 1H), 4.16-4.01 (m, 1H), 4.01-3.85 (m, 3H), 2.28 (s, 3H). |
| 6 | 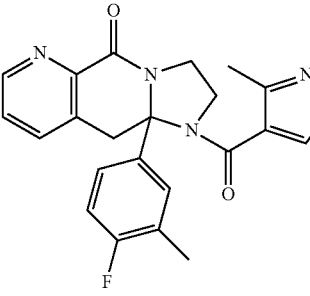 | ESI-MI m/z [M + H]+ 406.97. 1H NMR (400 MHz, CD3CN) δ 8.73 (s, 1H), 8.56 (ddd, J = 4.7, 1.5, 1.1 Hz, 1H), 7.81 (dt, J = 7.8, 1.2 Hz, 1H), 7.41 (dd, J = 7.8, 4.7 Hz, 1H), 7.36 (dd, J = 7.3, 2.6 Hz, 1H), 7.31-7.23 (m, 1H), 6.93-6.85 (m, 1H), 4.73 (d, J = 16.1 Hz, 1H), 4.39-4.21 (m, 1H), 4.09-3.96 (m, 1H), 3.96-3.81 (m, 2H), 3.74 (d, J = 16.1 Hz, 1H), 2.28 (s, 3H), 2.16 (d, J = 1.9 Hz, 3H). |

-continued

| Cpd. No. | Structure | ESI-MI m/z [M + H]+/1H-NMR |
|---|---|---|
| 7 | 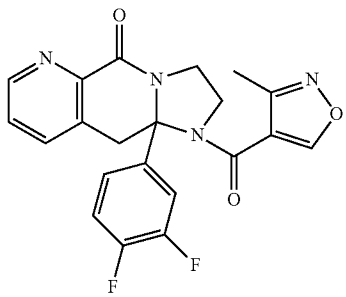 [SMILES: Cc1nocc1C(=O)N1CCN2C(=O)c3ncccc3CC12c1ccc(F)c(F)c1] | ESI-MI m/z [M + H]+ 410.96. 1H NMR (400 MHz, CD3CN) δ 8.78 (s, 1H), 8.59-8.52 (m, 1H), 7.84-7.78 (m, 1H), 7.50 (ddd, J = 12.3, 7.6, 2.5 Hz, 1H), 7.41 (dd, J = 7.8, 4.7 Hz, 1H), 7.25-7.18 (m, 1H), 7.15-7.04 (m, 1H), 4.71 (d, J = 16.2 Hz, 1H), 4.38-4.28 (m, 1H), 4.11-3.99 (m, 1H), 3.96-3.84 (m, 2H), 3.75 (d, J = 16.2 Hz, 1H), 2.29 (s, 3H). |
| 8 | 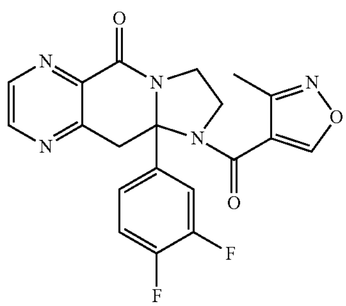 [SMILES: Cc1nocc1C(=O)N1CCN2C(=O)c3nccnc3CC12c1ccc(F)c(F)c1] | ESI-MI m/z [M + H]+ 411.89. 1H NMR (400 MHz, Acetone) δ 9.14 (s, 1H), 8.69 (d, J = 2.4 Hz, 1H), 8.64 (dd, J = 2.3, 1.0 Hz, 1H), 7.56 (ddd, J = 12.1, 7.6, 2.4 Hz, 1H), 7.34-7.17 (m, 2H), 4.88 (d, J = 16.6 Hz, 1H), 4.50-4.41 (m, 1H), 4.41-4.30 (m, 1H), 4.25 (ddd, J = 9.8, 8.1, 4.2 Hz, 1H), 4.10 (d, J = 16.6 Hz, 1H), 4.08-3.98 (m, 1H), 2.34 (s, 3H). |
| 9 | 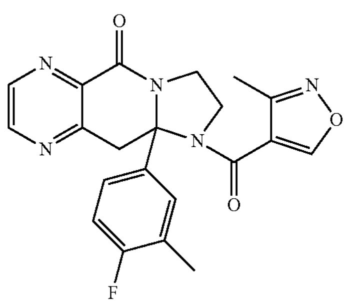 [SMILES: Cc1cc(C23Cc4nccnc4C(=O)N2CCN3C(=O)c2conc2C)ccc1F] | ESI-MI m/z [M + H]+ 407.89. 1H NMR (400 MHz, Acetone) δ 9.11 (s, 1H), 8.66 (d, J = 2.4 Hz, 1H), 8.61 (dd, J = 2.4, 1.1 Hz, 1H), 7.44 (ddd, J = 7.2, 2.7, 0.5 Hz, 1H), 7.37-7.29 (m, 1H), 6.95 (t, J = 9.1 Hz, 1H), 4.91 (d, J = 16.6 Hz, 1H), 4.41 (ddd, J = 11.4, 8.5, 4.3 Hz, 1H), 4.32 (ddd, J = 9.8, 8.5, 6.7 Hz, 1H), 4.18 (ddd, J = 9.8, 8.2, 4.3 Hz, 1H), 4.07 (dd, J = 16.6, 0.9 Hz, 1H), 4.01 (ddd, J = 11.4, 8.2, 6.7 Hz, 1H), 2.34 (s, 3H), 2.16 (d, J = 1.9 Hz, 3H). |
| 10 | 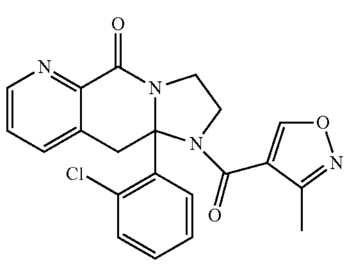 [SMILES: Cc1nocc1C(=O)N1CCN2C(=O)c3ncccc3CC12c1ccccc1Cl] | ESI-MI m/z [M + H]+ 408.93. 1H NMR (400 MHz, CDCl3) δ 8.70-8.63 (m, 1H), 8.52 (s, 1H), 7.66-7.56 (m, 1H), 7.38 (dd, J = 7.9, 1.3 Hz, 1H), 7.35 (dd, J = 7.7, 4.7 Hz, 1H), 7.24 (dd, J = 8.0, 1.6 Hz, 1H), 7.19 (td, J = 7.7, 1.6 Hz, 1H), 7.11-7.02 (m, 1H), 4.64 (d, J = 16.4 Hz, 1H), 4.32-4.18 (m, 2H), 4.12-3.98 (m, 2H), 3.79-3.62 (m, 1H), 2.42 (s, 3H). |
| 11 | 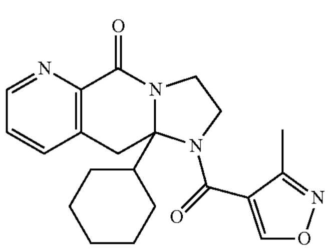 [SMILES: Cc1nocc1C(=O)N1CCN2C(=O)c3ncccc3CC12C1CCCCC1] | ESI-MI m/z [M + H]+ 381.04. 1H NMR (400 MHz, CDCl3) δ 8.75-8.64 (m, 1H), 8.61 (s, 1H), 7.65-7.55 (m, 1H), 7.39 (dd, J = 7.7, 4.7 Hz, 1H), 4.57 (ddd, J = 12.0, 8.4, 3.5 Hz, 1H), 4.34 (d, J = 16.9 Hz, 1H), 3.96-3.86 (m, 2H), 3.86-3.75 (m, 1H), 3.48 (d, J = 16.8 Hz, 1H), 2.60-2.49 (m, 1H), 2.47 (s, 3H), 1.78-1.66 (m, 2H), 1.63-1.48 (m, 2H), 1.36-1.26 (m, 1H), 1.17-0.92 (m, 4H), 0.90-0.72 (m, 1H). |

| Cpd. No. | Structure | ESI-MI m/z [M + H]+/1H-NMR |
|---|---|---|
| 12 | 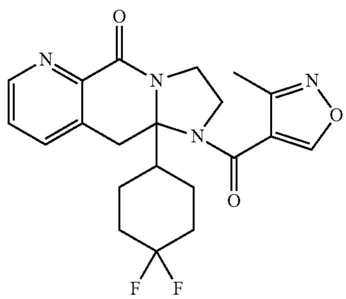 [SMILES: Cc1nocc1C(=O)N1CCN2C(=O)c3ncccc3CC12C1CCC(F)(F)CC1] | ESI-MI m/z [M + H]+ 417.13. 1H NMR (400 MHz, CDCl3) δ 8.76 (d, J = 4.4 Hz, 1H), 8.64 (s, 1H), 7.64 (d, J = 7.7 Hz, 1H), 7.44 (dd, J = 7.7, 4.7 Hz, 1H), 4.61 (ddd, J = 12.1, 8.5, 3.5 Hz, 1H), 4.38 (d, J = 16.9 Hz, 1H), 4.04-3.85 (m, 2H), 3.85-3.69 (m, 1H), 3.51 (d, J = 16.8 Hz, 1H), 2.68-2.57 (m, 1H), 2.47 (s, 3H), 2.14-2.03 (m, 1H), 2.03-1.89 (m, 1H), 1.81-1.12 (m, 6H). |
| 13 | 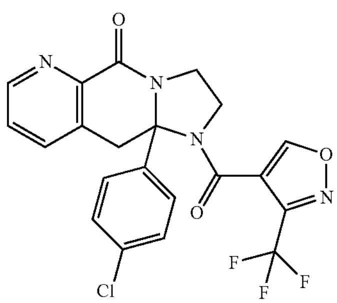 [SMILES: O=C(c1conc1C(F)(F)F)N1CCN2C(=O)c3ncccc3CC12c1ccc(Cl)cc1] | ESI-MI m/z [M + H]+ 463. 1H NMR (400 MHz, Acetone) δ 9.96 (s, 1H), 9.03-8.95 (m, 1H), 8.40-8.29 (m, 1H), 8.01 (d, J = 8.9 Hz, 2H), 7.89 (dd, J = 7.7, 4.7 Hz, 1H), 7.75 (d, J = 8.9 Hz, 2H), 5.21 (d, J = 16.0 Hz, 1H), 4.84 (ddd, J = 11.5, 8.6, 4.7 Hz, 1H), 4.70 (ddd, J = 9.9, 8.6, 6.5 Hz, 1H), 4.50 (ddd, J = 10.0, 8.2, 4.7 Hz, 1H), 4.39 (ddd, J = 11.5, 8.2, 6.5 Hz, 1H), 4.27 (d, J = 16.0 Hz, 1H). |
| 14 | 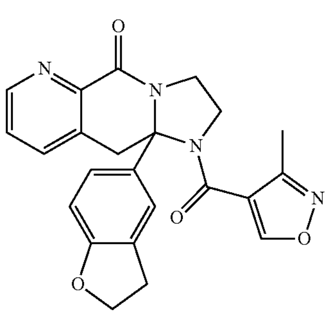 [SMILES: Cc1nocc1C(=O)N1CCN2C(=O)c3ncccc3CC12c1ccc2c(c1)CCO2] | ESI-MI m/z [M + H]+ 416.15. 1H NMR (400 MHz, CDCl3) δ 8.65 (d, J = 4.6 Hz, 1H), 8.47 (s, 1H), 7.58 (d, J = 7.7 Hz, 1H), 7.32 (dd, J = 7.7, 4.7 Hz, 1H), 7.30-7.28 (m, 1H), 7.24 (dd, J = 8.5, 2.2 Hz, 1H), 6.61 (d, J = 8.5 Hz, 1H), 4.72 (d, J = 16.0 Hz, 1H), 4.50 (t, J = 8.8 Hz, 2H), 4.47-4.37 (m, 1H), 4.07-3.94 (m, 2H), 3.83 (d, J = 16.0 Hz, 1H), 3.80-3.71 (m, 1H), 3.09 (t, J = 8.7 Hz, 2H), 2.43 (s, 3H). |

Separation of Stereoisomers by Chiral Chromatography

Representative compound examples 1, 2, 4, 5 and 6 were prepared as their single enantiomers 1A, 2A, 2B, 4A, 5A and 6A by separating their precursors of formula (II) (which may be synthesised according to steps 1 and 2 of General Method A) into single enantiomers followed by acylation as generally described in step 3 of General Method A. The separation of enantiomers was achieved by HPLC using chromatographic columns with a chiral stationary phase. For example, the following racemic compounds of general formula (II) were separated into their enantiomers (designated A and B) under the conditions detailed in Table 1 below.

TABLE 1

HPLC Enantiomeric Separation Conditions for representative compounds of formula (II)

| Compound of Formula (II) (Racemate) | Chiral HPLC Conditions | Retention Time of Enantiomers (min) B | A | Enantiomeric Compound of Formula (I) Example No[a] |
|---|---|---|---|---|
| 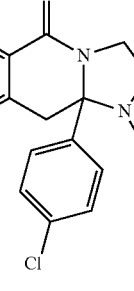 (i) | Column: Chiralpak IC 250 × 4.6 mm<br>Eluent: Hexane:EtOH 60:40 (v/v)<br>Flow rate: 1.5 mL/min<br>Temperature: Ambient<br>Concentration: 1.0 mg/mL<br>Injection vol: 20 uL<br>UV Detection: 254 nm | 6.6 | 9.8 | (1A) |
| 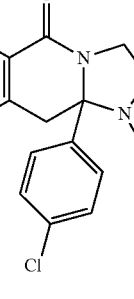 (ii) | Column: Chiralpak AD-H 250 × 10 mm<br>Eluent: Hexane:IPA 70:30 (v/v)<br>Flow rate: 4.0 mL/min<br>Temperature: Ambient<br>Concentration: 1 mg/mL<br>Injection vol: 100 uL<br>UV Detection: 214, 230, 254, 280, 500 nm | 8.7 | 9.3 | (2A) (2B) |
| 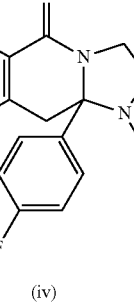 (iv) | Column: Chiralpak AD-H 250 × 4.6 mm<br>Eluent: Hexane:IPA 80:20 (v/v)<br>Flow rate: 1.5 mL/min<br>Temperature: Ambient<br>Concentration: 1.0 mg/mL<br>Injection vol: 10 uL<br>UV Detection: 220 nm | 7.4 | 8.9 | (4A) |
| 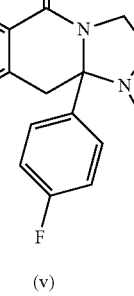 (v) | Column: Chiralpak AD-H 250 × 4.6 mm<br>Eluent: Hexane:IPA 80:20 (v/v)<br>Flow rate: 1.5 mL/min<br>Temperature: Ambient<br>Concentration: 1.0 mg/mL<br>Injection vol: 10 uL<br>UV Detection: 220 nm | 7.2 | 10.5 | (5A) |

TABLE 1-continued

HPLC Enantiomeric Separation Conditions for representative compounds of formula (II)

| Compound of Formula (II) (Racemate) | Chiral HPLC Conditions | Retention Time of Enantiomers (min) B | A | Enantiomeric Compound of Formula (I) Example No[a] |
|---|---|---|---|---|
| (vi) | Column: Chiralcel OD-H 250 × 4.6 mm Eluent: Hexane:EtOH 60:40 (v/v) Flow rate: 1.5 mL/min Temperature: Ambient Concentration: 1 mg/mL Injection vol: 10 uL UV Detection: 220 nm | 3.4 | 6.2 | (6A) |

[a] In the case of enantiomeric compound examples 1A, 2A, 4A, 5A and 6A of formula (I) as described in Table 4 below, enantiomer A of formula (II) is subjected to acylation step 3 of General Method A to yield the final compound. In the case of enantiomeric compound example 2B of formula (I) as described in Table 4 below, enantiomer B of formula (II) is similarly subjected to acylation step 3 of General Method A to yield the final compound.

It will be understood that chiral HPLC methods may also be used to separate the enantiomers of compounds of formula (I) under appropriate conditions, for example, similar to those described in Table 1.

Synthesis of Stereoisomers by Diastereomeric Salt Formation Using a Chiral Acid

Diastereomeric Salt Formation:

Generally, to a solution of a racemic compound of formula (II) in an appropriate solvent (such as methanol, ethanol or 2-propanol) or solvent combination (such as methanol, 2-propanol and ethyl acetate 1:1:1) was added (R)-(−) or (S)-(+)-1,1'-binaphthyl-2,2'-diyl hydrogen phosphate (BNPPA) (1 equiv). The mixture was then stirred at room temperature or heated at a temperature up to 50° C. until a clear solution formed. Heating was continued for 1 hr then cooled gradually to room temperature. The precipitated diasteromeric salt was filtered and washed with the same solvent (or solvent combination) then air dried at atmospheric temperature. The filtered mother liquor was concentrated to 50% of its original volume and cooled to room temperature. The precipitated solids were filtered and the filtrate chilled to −5 to 0° C. for approximately 2 hrs and further precipitated solids were collected again. The sequence was repeated with the enantiomer (A or B) and chiral purity determined by chiral HPLC after each filtration.

Conversion of Diastereomeric Salt into Free Base:

To a suspension of the distereomeric salt in water and dichloromethane (1:1) was added a saturated solution of sodium bicarbonate (sufficient to adjust the pH to approximately 8) and the mixture was stirred for approximately 30 minutes. The precipitated solid was filtered and washed with dichloromethane. The organic layer in the filtrate was separated and the aqueous extracted with dichloromethane. The combined organic layers were washed with saturated sodium bicarbonate, dried over anhydrous sodium sulfate and concentrated to give the separated enantiomer (A or B) with chiral purity determined by chiral HPLC as described previously.

Representative Compound Example 4A was made using the diastereomeric salt formation method as follows.

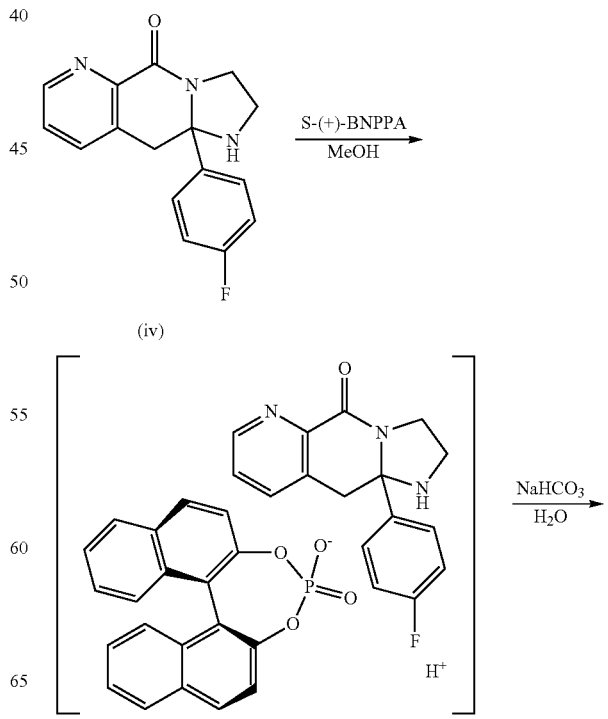

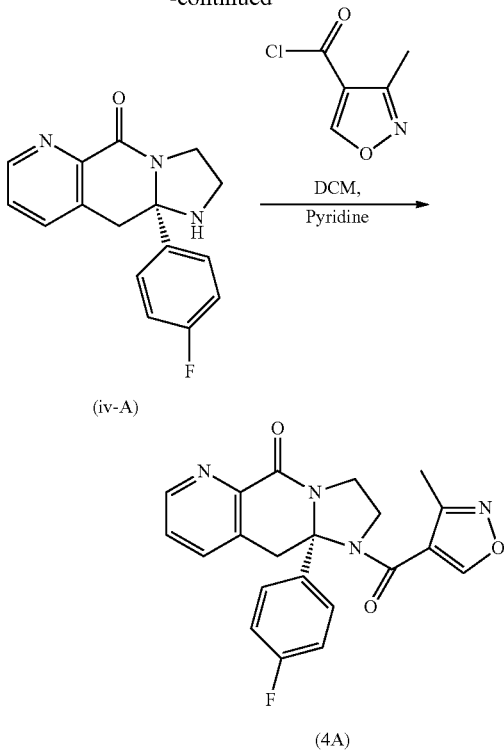

To a stirred solution of the racemic core (iv) (5 g, 17 mmol, 1 eq) in methanol (100 mL) was added (S)-(+)-BNPPA (6.1 g, 17 mmol, 1 eq) at room temperature. The reaction mixture became clear in approximately 20 minutes and a salt slowly precipitated out after 3 h. The resultant suspension was stirred for a further 4 h and the resultant solid was filtered and washed with methanol (25 mL). The isolated crude salt (~5.5 g) was suspended in methanol (27 mL) and stirred at 50-55° C. for 30 min. The resultant slurry was filtered and washed with methanol (20 mL). This process was repeated three times to give the diastereomeric salt as an off-white solid (3 g, 27%, with a chiral purity of 99.6% ee as determined by chiral HPLC of the free base). Conversion of the diastereomeric salt to the free base (iv-A) was performed as previously described followed by acylation to give compound (4A).

Biological Data

The in vivo and in vitro antiviral activity of the compounds of the invention may be determined using the following methods.

RSV Antiviral Assay Protocol

Compounds of the invention were tested for their antiviral activity against respiratory syncytial virus. Cytopathic effect (CPE) assays were performed essentially as described in the literature (see for example Watanabe et al, 1994, J. Virological Methods, 48:257). Serial dilutions of the test compounds were made in 96 well plates. HEp2 cells ($1.0 \times 10^4$ cells/well) were infected with RSV at a low multiplicity of infection (e.g. RSV A2 at an moi of ~0.01) and added to plates to assess antiviral activity. Uninfected HEp2 cells were used to assess compound cytotoxicity. Assays were incubated for 5 days at 37° C. in a 5% $CO_2$ atmosphere. The extent of CPE was determined via metabolism of the vital dye 3-(4,5-dimethylthiazol-2-yl)-2,5-diphenyltetrazolium bromide (MTT). MTT (1 mg/ml) was added to each well and plates incubated for 2 hours incubation at 37° C. Wells were aspirated, isopropanol (200 μL) was added and absorbance values read at 540/650 nm. Compound concentrations that inhibited CPE by 50% ($EC_{50}$) and developed cytotoxicity ($CC_{50}$) were calculated using non-linear regression analysis. The $EC_{50}$ values are shown in Tables 2 and 4 below. The $CC_{50}$ values of the compounds tested were determined to be >5000 nM.

RSV Antiviral Assay in the Presence of a Human Serum Protein

A CPE inhibition assay was used to quantify the effect of test compounds on RSV-induced CPE in cell culture in the presence of alpha-1-acid glycoprotein (AAG; Sigma Aldrich, cat #G9885) or human serum albumin (HSA; Sigma Aldrich A1653). Serial dilutions of the test compounds were made in 96 well plates in media supplemented with 1.5 mg/mL of AAG or 2% HSA. HEp-2 cells ($1.0 \times 10^4$ cells/well) were infected by RSV A2 at a low multiplicity of infection (MOI ~0.01) and added to plates to assess antiviral activity in the presence of serum protein AAG or HSA. Assays were incubated at 37° C. in a humidified 5% $CO_2$ atmosphere for five days. The extent of CPE was determined via metabolism of the vital dye 3-(4,5-dimethylthiazol-2-yl)-2,5-diphenyl-tetrazolium bromide (MTT). MTT (1 mg/mL) was added to the cells and plates followed by a two hour incubation at 37° C. in a humidified 5% $CO_2$ atmosphere. Wells were aspirated, isopropanol (200 uL) was added and absorbance values read at 540/650 nm. Compound concentrations that inhibited CPE by 50% ($EC_{50}$) were calculated using non-linear regression analysis.

The $EC_{50}$ values of test compounds in the presence of 1.5 mg/mL of AAG or 2% HSA were compared to $EC_{50}$ values without the plasma protein to generate fold shifts, a compound was considered to be affected by the presence of the plasma protein if the activity shift was >10 fold. The activity shift of the compounds tested was determined to be <10 fold.

For example, compound 2 was tested in the assay and the AAG fold shift determined to be 3.3. The active enantiomer of compound 2, namely compound 2A was also tested and the AAG fold shift determined to be 2.9.

RSV Fusion Assay

Compounds of the invention can be tested for their ability to inhibit the essential fusion processes of the respiratory syncytial virus.

Generation of RSV-F Constructs

Single-stranded synthetic DNA oligonucleotides encoding the portions of RSV A2 F glycoprotein incorporating optimal codons and without potential poly(A) addition or splice sites are generated synthetically (Mason et al, WO0242326). A membrane-anchored full-length F may be generated essentially according to the method described therein and in Morton et al.

Syncytium Formation Assay

Fusion activity of the RSV-F constructs may be measured in 293 cells essentially according to the method described in Morton et al, 2003, Virology, 311:275. For example: cells in six well plates at approximately 80% confluency are transfected by adding plasmid DNA (0.5-1.5 μg/well) carrying the constructs of interest in $CaPO_4$ solution for 2 hours. After glycerol shock and wash, the transfected cells are trypsinized and $4-10 \times 10^4$ cells/well added to 96-well plates containing 2-fold or 3-fold serial dilutions of the test compound. Syncytium formation is evaluated by visual inspection and quantified at 42 hours post-transfection by addition of 20 μL of CellTiter 96 One Solution (Promega) followed by incubation for 2 hours at 37° C. The absorbance values read at 492/690 nm. The compound concentration that reduced absorbance relative to untreated control cultures by 50% ($EC_{50}$) is calculated using non-linear regression analysis.

Plasma Protein Binding Assay

Compounds of the invention were tested for the extent of protein binding in human and animal plasma. Stock solutions of test compounds were prepared in dimethyl sulfoxide (DMSO) at a concentration of 10 mg/mL. These stock solutions were initially diluted to 1.0 mg/mL using DMSO, and then further diluted using 1:1 (v/v) acetonitrile/water to prepare spiking solutions at nominal concentrations of 20 and 200 μg/mL. Aliquots of human, rat or dog plasma (maintained at 37° C.) were spiked with the spiking solution to give nominal plasma concentrations of 200 and 2000 ng/mL (maximum final DMSO and acetonitrile concentrations were 0.2% (v/v) and 0.5% (v/v), respectively). The spiked plasma tubes were allowed to equilibrate at 37° C. for 60 minutes. Aliquots of spiked plasma (230 μL) were then transferred into ultracentrifuge tubes and subjected to ultracentrifugation (Beckman Rotor type 42.2 Ti; 42,000 rpm and 37° C.) for 4.2 h to separate plasma proteins from plasma water. Following ultracentrifugation, a 50 μL aliquot of supernate (i.e. plasma water) was taken from each tube for determination of the concentration of test compound by LCMS.

The total concentration of each test compound was determined in samples of unspun plasma that were incubated at 4° C. and 37° C. for the duration of the ultracentrifugation run (i.e. 4.2 h). The potential for compound degradation during the ultracentrifugation run was assessed by comparing the concentration of each test compound in unspun plasma that was maintained at 37° C. with that in unspun plasma that was maintained at 4° C. The concentration of each test compound in samples of plasma-water and unspun plasma was determined by LC-MS. The LLQ values generally ranged between 0.5-5.0 ng/mL and 0.5-2.5 ng/mL in plasma and in plasma-water, respectively. Based on the concentrations observed in unspun plasma maintained at 37° C. (Cplasma) and plasma water (Cplasma-water), the percentage of compound bound to plasma proteins (% bound) was calculated according to the following equation: % bound=[(Cplasma−Cplasma-water)/Cplasma]×100.

A compound is considered to have low protein binding when % bound is <95%. The % bound of the compounds tested was <95% in human, rat and dog plasma at nominal plasma concentrations of 200 and 2000 ng/mL.

hERG Ion Channel Inhibition (ScreenPatch® Assay)

The effects of compounds of the invention on the on hERG ion channel can be evaluated using an IonWorks Quattro™ system essentially as described in the literature (see for example Bridgland-Tayor et al, 2006, J. Pharmacological and Toxicological Methods 54: 189).

Four compound concentrations were applied to naïve cells via steel needles of a 48-channel pipettor. Each application consisted of addition of 6 μL of 2× concentrated test compounds to the total of 12 μL of final volume of the extracellular well of the Population Patch Clamp™ (PPC) planar electrode. Duration of exposure to each test compound concentration was at least five minutes.

Intracellular solution was loaded into the intracellular compartment of the PPC planar electrode. Cell suspensions (CHO cells stably transfected with hERG cDNA) are pipetted into the wells of the PPC planar electrode. After establishment of a whole-cell configuration, membrane currents were recorded using patch clamp amplifier in the IonWorks Quattro™ system. Two recordings of the ion channel currents were performed (before and 5 minutes after test compound application). hERG current was measured using a pulse pattern with fixed amplitudes (conditioning prepulse: −80 mV for 25 ms; test pulse +40 mV for 80 ms) from a holding potential of 0 mV. hERG current was measured as a difference between the peak current at 1 ms after the test step to +40 mV and the steady state current at the end of the step to +40 mV.

Data acquisition and analyses was performed using the IonWorks Quattro™ system operation software. The decrease in current amplitude after test compound application was used to calculate the percent block relative to control. A compound is considered to have a low hERG inhibition when the hERG $IC_{50}$ is >500 times higher than the RSV A2 $EC_{50}$. The hERG $IC_{50}$ of the compounds tested was >500 times higher than the corresponding RSV A2 $EC_{50}$ values.

For example, compound 2 was tested in the assay and the % hERG inhibition at 100 μM determined to be 50.2 with a hERG $IC_{50}$ of 99.2 μM. The active enantiomer of compound 2, namely compound 2A was also tested and the % hERG inhibition at 100 μM determined to be 41.4 with a hERG $IC_{50}$ of 129.5 μM.

RSV Cotton Rat Model

The cotton rat model may be performed essentially as described in the literature (Wyde et al, 2003, Antiviral Res., 60:221). Briefly, cotton rats weighing 50-100 g are lightly anesthetized with isoflurane and dosed orally with compound or vehicle control and subsequently on a daily or twice daily basis. Viral infection follows 2 hours post-treatment in similarly anesthetized rats by intranasal instillation with approximately 1000 $TCID_{50}$ of RSV A2 per animal. Four days after virus inoculation, each cotton rat is sacrificed and their lungs removed and RSV titres determined by plaque assay.

RSV Balb/c Mouse Model

The mouse model may be performed essentially as described by Cianci et al, 2004, Antimicrobial Agents and Chemotherapy., 48:413. Briefly, eight week old female Balb/c mice are weighed, anesthetized intraperitoneally with Avertin™ and compound or vehicle administered orally pre-infection and subsequently on a daily or twice daily basis. Mice are inoculated intranasally with approximately 10000 $TCID_{50}$ RSV A2 per animal. Three days after virus inoculation, each mouse is sacrificed and their lungs removed and RSV titres determined by plaque assay. Body weights, spleen and liver weights can also be assessed. In addition, the ability of a test compound to reduce total and differential (macrophages, neutrophils and lymphocytes) inflammatory cell counts in bronchoalveolar lavage fluid (BALF) can also be measured. This allows a study of the ability of the test compound to ameliorate the inflammatory response to RSV infection in animals treated with compound compared with those only inoculated with RSV.

Aqueous Solubility

Test compounds prepared in DMSO were screened in duplicate over a range of concentrations (1.6-100 ug/mL) in different aqueous media (for example pH2 or pH6.5 buffers which are relevant to the stomach and upper regions of the small intestine). Test compounds were serially diluted in 100% DMSO ranging from 10-0.16 mg/mL. These diluted compounds were then added to test plates (UV Star Griener 96 well plates) containing assay buffers with a further 1:100 dilution keeping a constant 1% DMSO concentration across the plate. The solubility concentration range was determined by interpreting NEPHELOstar laser nephelometery readings taken after a 30 minute incubation at 25° C. The results are shown in Tables 3 and 4 below. A compound is considered to have good solubility when the value is >25 ug/mL. The solubility of the compounds tested was determined to be >25 ug/mL at both pH2 and pH6.5.

RSV Activity and Solubility Data

In order to demonstrate the desirable properties and advantages of compounds of formula (I), the inventors performed comparative activity and solubility assays as against a structurally related subclass of compounds in WO2008/037011. Comparator compound A, having a substituent in the 5-position, was also made and its activity tested. The results are provided in Tables 2 and 3. The inventors found that, surprisingly the unsubstituted isoxazol-3-yl (Compound 1-806) and isoxazol-5-yls (Compounds 1-025, 1-088 and 1-100) of WO2008/037011 were less active and less soluble that the 3-substituted isoxazol-4-yls of the present invention and further, a ten-fold drop in activity was observed when the activity of the 5-substituted isoxazol-4-yl (Compound A) was directly measured against the 3-substituted isoxazol-4-yl compound of example 4.

Accordingly, the inventors believe, without wishing to be bound by theory, that one or more advantages, of the present invention are realised, at least in part, by the compounds comprising an isoxazol-4-yl with a substituent in the 3-position.

TABLE 2

| | RSV A2 Antiviral $EC_{50}$ | | |
|---|---|---|---|
| Compound Structure | Compound Subclass | Compound No. | RSV A2 $EC_{50}$ (nM) |
| | Unsubstituted isoxazol-5-yl | 1-025[a] | 1708.5 |
| | Unsubstituted isoxazol-3-yl | 1-086[a] | 175.2 |
| | Unsubstituted isoxazol-5-yl | 1-088[a] | 267.4 |
| | Unsubstituted isoxazol-5-yl | 1-100[a] | 559.9 |

TABLE 2-continued

RSV A2 Antiviral EC$_{50}$

| Compound Structure | Compound Subclass | Compound No. | RSV A2 EC$_{50}$ (nM) |
|---|---|---|---|
| 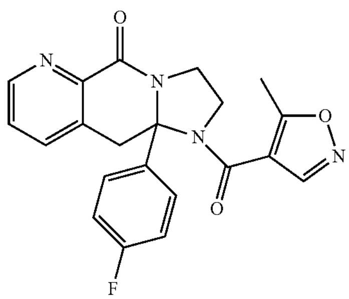 [SMILES: Cc1oncc1C(=O)N1CCN2C(=O)c3ncccc3CC12c1ccc(F)cc1] | 5-substituted isoxazol-4-yl | A | 276.3 |
| | 3-substituted isoxazol-4-yl | 1 | 6.3 |
| | 3-substituted isoxazol-4-yl | 2 | 5.2 |
| | 3-substituted isoxazol-4-yl | 3 | 83.1 |
| | 3-substituted isoxazol-4-yl | 4 | 27.5 |

TABLE 2-continued

| Compound Structure | Compound Subclass | Compound No. | RSV A2 EC$_{50}$ (nM) |
|---|---|---|---|
| | 3-substituted isoxazol-4-yl | 5 | 27.6 |
| | 3-substituted isoxazol-4-yl | 6 | 6.4 |
| | 3-substituted isoxazol-4-yl | 7 | 35 |
| | 3-substituted isoxazol-4-yl | 8 | 30.5 |
| | 3-substituted isoxazol-4-yl | 9 | 9 |

TABLE 2-continued
| | RSV A2 Antiviral EC$_{50}$ | | |
|---|---|---|---|
| Compound Structure | Compound Subclass | Compound No. | RSV A2 EC$_{50}$ (nM) |
| 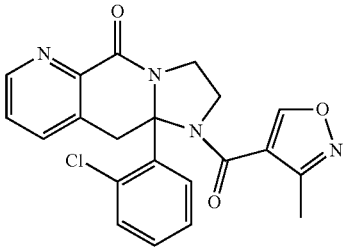 | 3-substituted isoxazol-4-yl | 10 | 36.9 |
| 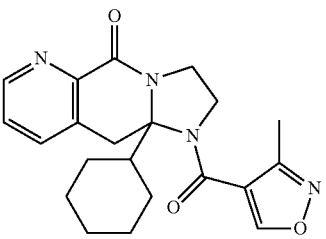 [SMILES: Cc1nocc1C(=O)N1CCN2C(=O)c3ncccc3CC12C1CCCCC1] | 3-substituted isoxazol-4-yl | 11 | 70 |
| 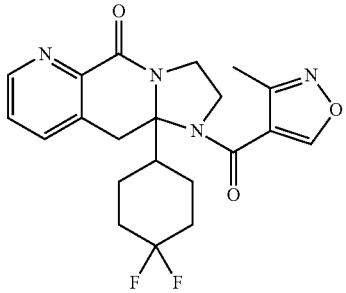 [SMILES: Cc1nocc1C(=O)N1CCN2C(=O)c3ncccc3CC12C1CCC(F)(F)CC1] | 3-substituted isoxazol-4-yl | 12 | 64.4 |
| 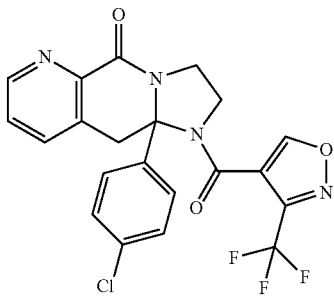 [SMILES: O=C(c1conc1C(F)(F)F)N1CCN2C(=O)c3ncccc3CC12c1ccc(Cl)cc1] | 3-substituted isoxazol-4-yl | 13 | 7 |
| 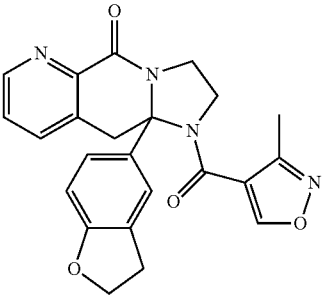 [SMILES: Cc1nocc1C(=O)N1CCN2C(=O)c3ncccc3CC12c1ccc2c(c1)CCO2] | 3-substituted isoxazol-4-yl | 14 | 13.6 |
[a] Compound number according to WO2008/037011.

TABLE 3

Solubility Data

| Compound No. | Solubility at pH2 (μg/mL) | Solubility at pH6.5 (μg/mL) | Compound No. | Solubility at pH2 (μg/mL) | Solubility at pH6.5 (μg/mL) |
|---|---|---|---|---|---|
| 1-025 | 3.1-6.3 | 3.1-6.3 | 1-086 | <1.6 | <1.6 |
| 1-088 | 3.1-6.3 | 3.1-6.3 | 1 | 50-100 | 50-100 |
| 2 | 50-100 | >100 | 3 | >100 | >100 |
| 4 | >100 | >100 | 5 | >100 | >100 |
| 6 | 25-50 | 50-100 | 7 | 25-50 | 50-100 |
| 8 | >100 | >100 | 9 | 50-100 | >100 |
| 10 | >100 | >100 | 11 | >100 | >100 |
| 12 | 50-100 | >100 | 13 | 50-100 | 50-100 |
| 14 | >100 | 50-100 | | | |

The enantiomeric antiviral activity and solubility of selected compounds of the invention was also determined and the results are shown in Table 4.

TABLE 4

RSV A2 Antiviral EC$_{50}$ and Solubility of Enantiomers

| Structure | Compound No | RSV A2 EC$_{50}$ (nM) | Solubility at pH 2 (μg/mL) | Solubility at pH 6.5 (μg/mL) |
|---|---|---|---|---|
| 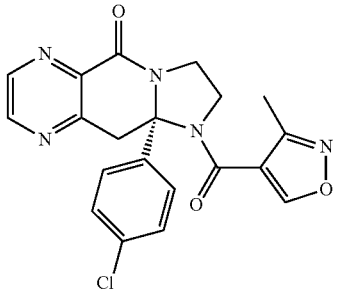 [SMILES: Cc1nocc1C(=O)N1CCN2C(=O)c3nccnc3C[C@]12c1ccc(Cl)cc1] | 1A | 5.2 | 50-100 | >100 |
| 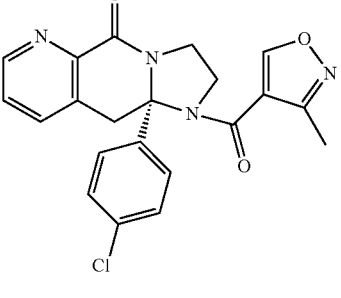 | 2A | 4.1 | 50-100 | >100 |
| 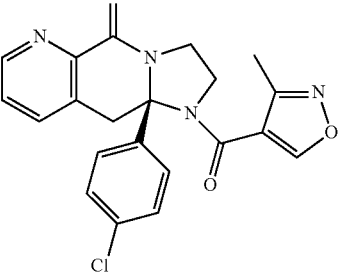 | 2B | 5000 | ND | ND |
| 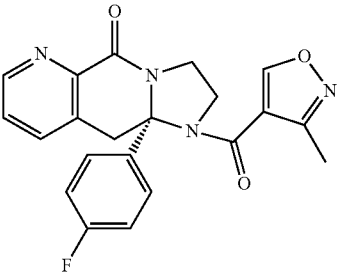 [SMILES: Cc1nocc1C(=O)N1CCN2C(=O)c3ncccc3C[C@]12c1ccc(F)cc1] | 4A | 16.3 | >100 | >100 |

TABLE 4-continued

| | | | Solubility | Solubility |
| Structure | Compound No | RSV A2 EC$_{50}$ (nM) | at pH 2 (µg/mL) | at pH 6.5 (µg/mL) |
|---|---|---|---|---|
| 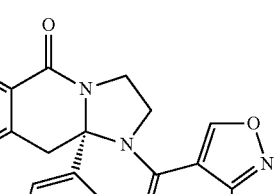 | 5A | 12.4 | >100 | >100 |
| 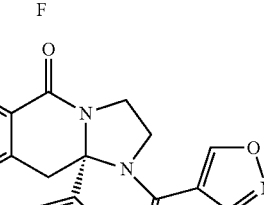 | 6A | 7.7 | 50-100 | >100 |

ND is "Not Determined"

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication, or information derived from it, or to any matter which is know, is not, and should not be taken as an acknowledgement or admission or any form of suggestion that that prior publication, or information derived from it, or known matter forms part of the common general knowledge in the field of endeavour to which this specification relates.

The invention claimed is:

1. A compound of formula (I), racemates, stereoisomers and/or salts thereof:

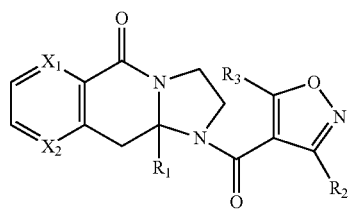

(I)

wherein
$X_1$ is N and $X_2$ is CH;
$R_1$ is selected from a carbocyclic ring, a heterocyclic ring, an aromatic ring, a substituted carbocyclic ring, a substituted heterocyclic ring, and a substituted aromatic ring, wherein the substituent is one or more groups selected from $C_{1-6}$alkyl, $C_{2-6}$alkenyl, $C_{2-6}$alkynyl, aryl, halogen, halo $C_{1-6}$alkyl, halo$C_{2-6}$alkenyl, halo$C_{2-6}$alkynyl, haloaryl, hydroxyl, $C_{1-6}$alkylhydroxy, $C_{1-6}$alkoxy, —O$C_{1-6}$alkylhydroxy, —O$C_{1-6}$alkyl$C_{1-6}$alkoxy, $C_{2-6}$alkenyloxy, aryloxy, benzyloxy, halo$C_{1-6}$alkoxy, halo$C_{2-6}$alkenyloxy, haloaryloxy, nitro, nitro$C_{1-6}$alkyl, nitro$C_{2-6}$alkenyl, nitro$C_{2-6}$alkynyl, nitroaryl, nitroheterocyclyl, amino, $C_{1-6}$alkylamino, $C_{1-6}$dialkylamino, $C_{2-6}$alkenylamino, $C_{2-6}$alkynylamino, arylamino, diarylamino, benzylamino, dibenzylamino, acyl, $C_{2-6}$alkenylacyl, $C_{2-6}$alkynylacyl, arylacyl, acylamino, diacylamino, acyloxy, alkylsulphonyloxy, arylsulphonyloxy, heterocyclyl, heterocyclyloxy, heterocyclylamino, haloheterocyclyl, alkylsulphonyl, arylsulphonyl, mercapto, $C_{1-6}$alkylthio, benzylthio, and acylthio;
$R_2$ is selected from $C_{1-6}$alkyl, halo$C_{1-3}$alkyl and $C_{1-3}$alkoxy; and
$R_3$ is H, $C_{1-6}$alkyl, $C_{2-6}$alkenyl, $C_{2-6}$alkynyl, aryl, halogen, halo$C_{1-6}$alkyl, halo$C_{2-6}$alkenyl, halo$C_{2-6}$alkynyl, haloaryl, hydroxy, $C_{1-6}$alkylhydroxy, $C_{1-6}$alkoxy, —O$C_{1-6}$alkylhydroxy, —O$C_{1-6}$alkyl$C_{1-6}$alkoxy, $C_{2-6}$alkenyloxy, aryloxy, benzyloxy, halo$C_{1-6}$alkoxy, halo$C_{2-6}$alkenyloxy, haloaryloxy, nitro, nitro$C_{1-6}$alkyl, nitro$C_{1-6}$alkenyl, nitro$C_{1-6}$alkynyl, nitroC2-6alkenyl, nitroC2-6alkynyl, nitroaryl, nitroheterocyclyl, amino, $C_{1-6}$alkylamino, $C_{1-6}$dialkylamino, $C_{2-6}$alkenylamino, $C_{2-6}$alkynylamino, arylamino, diarylamino, benzylamino, dibenzylamino, acyl, $C_{2-6}$alkenylacyl, C2-6alkynylacyl, arylacyl, acylamino, diacylamino, acyloxy, alkylsulphonyloxy, arylsulphonyloxy, heterocyclyl, heterocyclyloxy, heterocyclylamino, haloheterocyclyl, alkylsulphonyl, arylsulphonyl, mercapto, $C_{1-6}$alkylthio, benzylthio, or acylthio.

2. The compound according to claim 1 of formula (Ia), racemates, stereoisomers and/or salts thereof:

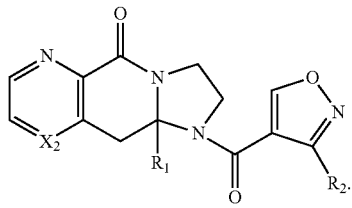

(Ia)

3. The compound according to claim 2 of formula (Ia-i) or salts thereof:

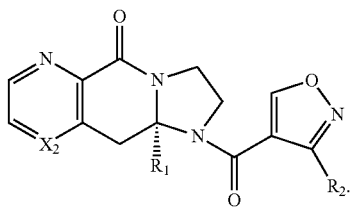

(Ia-i)

4. The compound according to claim 1 of formula (Ib), racemates, stereoisomers and/or salts thereof:

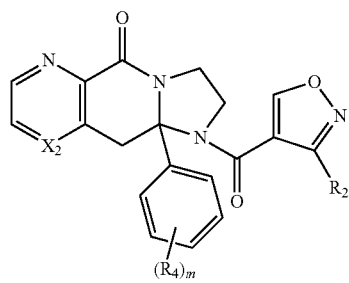

(Ib)

wherein m is an integer selected from 0, 1, 2 or 3; and $R_4$ is $C_{1-6}$alkyl, $C_{2-6}$alkenyl, $C_{2-6}$alkynyl, aryl, halogen, halo$C_{1-6}$alkyl, halo$C_{2-6}$alkenyl, halo$C_{2-6}$alkynyl, haloaryl, hydroxyl, $C_{1-6}$alkylhydroxy, $C_{1-6}$alkoxy, —O$C_{1-6}$alkylhydroxy, —O$C_{1-6}$alkyl$C_{1-6}$alkoxy, $C_{2-6}$alkenyloxy, aryloxy, benzyloxy, halo$C_{1-6}$alkoxy, halo$C_{2-6}$alkenyloxy, haloaryloxy, nitro, nitro$C_{1-6}$alkyl, nitro$C_{2-6}$alkenyl, nitro$C_{2-6}$alkynyl, nitroaryl, nitroheterocyclyl, amino, $C_{1-6}$alkylamino, $C_{1-6}$dialkylamino, $C_{2-6}$alkenylamino, $C_{2-6}$alkynylamino, arylamino, diarylamino, benzylamino, dibenzylamino, acyl, $C_{2-6}$alkenylacyl, $C_{2-6}$alkynylacyl, arylacyl, acylamino, diacylamino, acyloxy, alkylsulphonyloxy, arylsulphonyloxy, heterocyclyl, heterocyclyloxy, heterocyclylamino, haloheterocyclyl, alkylsulphonyl, arylsulphonyl, mercapto, $C_{1-6}$alkylthio, benzylthio, or acylthio.

5. The compound according to claim 4 of formula (Ib-i) or salts thereof:

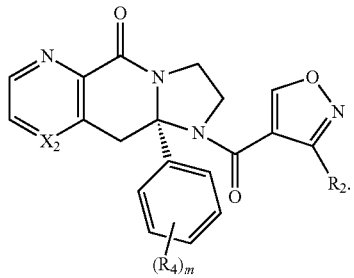

(Ib-i)

6. The compound according to claim 4, racemates, stereoisomers and/or salts thereof wherein $R_4$ is selected from the group consisting of $C_{1-3}$alkyl, halo$C_{1-3}$alkyl, halogen and $C_{1-3}$alkoxy.

7. The compound according to claim 1 of formula (Ic), racemates, stereoisomers and/or salts thereof:

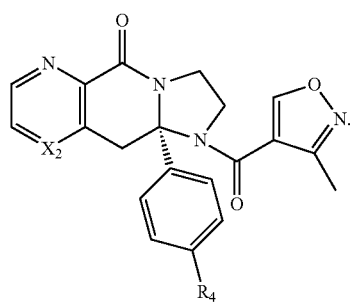

(Ic)

wherein $R_4$ is $C_{1-6}$alkyl, $C_{2-6}$alkenyl, $C_{2-6}$alkynyl, aryl, halogen, halo $C_{1-6}$alkyl, halo$C_{2-6}$alkenyl, halo$C_{2-6}$alkynyl, haloaryl, hydroxyl, $C_{1-6}$alkylhydroxy, $C_{1-6}$alkoxy, —O$C_{1-6}$alkylhydroxy, —O$C_{1-6}$alkyl$C_{1-6}$alkoxy, $C_{2-6}$alkenyloxy, aryloxy, benzyloxy, halo$C_{1-6}$alkoxy, halo$C_{2-6}$alkenyloxy, haloaryloxy, nitro, nitro$C_{1-6}$alkyl, nitro$C_{2-6}$alkenyl, nitro$C_{2-6}$alkynyl, nitroaryl, nitroheterocyclyl, amino, $C_{1-6}$alkylamino, $C_{1-6}$dialkylamino, $C_{2-6}$alkenylamino, $C_{2-6}$alkynylamino, arylamino, diarylamino, benzylamino, dibenzylamino, acyl, $C_{2-6}$alkenylacyl, $C_{2-6}$alkynylacyl, arylacyl, acylamino, diacylamino, acyloxy, alkylsulphonyloxy, arylsulphonyloxy, heterocyclyl, heterocyclyloxy, heterocyclylamino, haloheterocyclyl, alkylsulphonyl, arylsulphonyl, mercapto, $C_{1-6}$alkylthio, benzylthio, or acylthio.

8. The compound according to claim 7 of formula (Ic-i) or salts thereof:

(Ic-i)

9. The compound according to claim 7, wherein R$_4$ is C$_{1-3}$alkyl, halo C$_{1-3}$alkyl, halogen or C$_{1-3}$alkoxy.

10. The compound according to claim 1, racemates, stereoisomers and/or salts thereof wherein R$_1$ is selected from a 3-10 membered carbocyclic ring; a 9-10 membered fused bicyclic carbocyclic ring; a 5-6 membered monocyclic heterocyclic ring; a 9-10 membered fused bicyclic heterocyclic ring; a 6-membered aromatic ring; a substituted 3-10 membered carbocyclic ring; a substituted 9-10 membered fused bicyclic carbocyclic ring; a substituted 5-6 membered monocyclic heterocyclic ring; a substituted 9-10 membered fused bicyclic heterocyclic ring; and a substituted 6-membered aromatic ring.

11. The compound according to claim 10, racemates, stereoisomers and/or salts thereof wherein R$_1$ is selected from a C$_6$cycloalkyl, phenyl, a 5-6 membered monocyclic heterocyclic ring, a 9-membered fused bicyclic heterocyclic ring, a substituted C$_6$cycloalkyl, a substituted phenyl, a substituted 5-6 membered monocyclic heterocyclic ring, and a substituted 9-membered fused bicyclic heterocyclic ring.

12. The compound according to claim 1 in a single stereoisomeric form.

13. The compound according to claim 12 of formula (I-i) or salts thereof:

(I-i)

14. The compound according to claim 12 or salts thereof selected from the group consisting of:
(10aS)-10a-(4-chlorophenyl)-1-[(3-methyl-1,2-oxazol-4-yl)carbonyl]-2,3,10-,10a-tetrahydroimidazo[2,1-g][1,7]naphthyridin-5(1H)-one;
(10aS)-10a-(4-fluorophenyl)-1-[(3-methyl-1,2-oxazol-4-yl)carbonyl]-2,3,10-,10a-tetrahydroimidazo[2,1-g][1,7]naphthyridin-5(1H)-one; and
(10aS)-10a-(4-fluoro-3-methylphenyl)-1-[(3-methyl-1,2-oxazol-4-yl)carbony-1]-2,3,10,10a-tetrahydroimidazo[2,1-g][1,7]naphthyridin-5(1H)-one.

15. The compound according to claim 1, racemates, stereoisomers and/or salts thereof wherein R$_3$ is H.

16. The compound according to claim 1, racemates, stereoisomers and/or salts thereof selected from the group consisting of:
10a-(4-chlorophenyl)-1-[(3-methyl-1,2-oxazol-4-yl)carbonyl]-2,3,10,10a-tetrahydroimidazo[2,1-g][1,7]naphthyridin-5(1H)-one;
10a-(4-methoxyphenyl)-1-[(3-methyl-1,2-oxazol-4-yl)carbonyl]-2,3,10,10a-tetrahydroimidazo[2,1-g][1,7]naphthyridin-5(1H)-one;
10a-(4-fluorophenyl)-1-[(3-methyl-1,2-oxazol-4-yl)carbonyl]-2,3,10,10a-tetrahydroimidazo[2,1-g][1,7]naphthyridin-5(1H)-one;
10a-(4-fluoro-3-methylphenyl)-1-[(3-methyl-1,2-oxazol-4-yl)carbonyl]-2,3,-10,10a-tetrahydroimidazo[2,1-g][1,7]naphthyridin-5(1H)-one;
10a-(3,4-difluorophenyl)-1-[(3-methyl-1,2-oxazol-4-yl)carbonyl]-2,3,10,10-a-tetrahydroimidazo[2,1-g][1,7]naphthyridin-5(1H)-one;
10a-(2-chlorophenyl)-1-[(3-methyl-1,2-oxazol-4-yl)carbonyl]-2,3,10,10a-tetrahydroimidazo[2,1-g][1,7]naphthyridin-5(1H)-one;
10a-cyclohexyl-1-[(3-methyl-1,2-oxazol-4-yl)carbonyl]-2,3,10,10a-tetrahydroimidazo[2,1-g][1,7]naphthyridin-5(1H)-one;
10a-(4,4-difluorocyclohexyl)-1-[(3-methyl-1,2-oxazol-4-yl)carbonyl]-2,3,1-0,10a-tetrahydroimidazo[2,1-g][1,7]naphthyridin-5(1H)-one;
10a-(4-chlorophenyl)-1-{[3-(trifluoromethyl)-1,2-oxazol-4-yl]carbonyl}-2,-3,10,10a-tetrahydroimidazo[2,1-g][1,7]naphthyridin-5(1H)-one;
10a-(2,3-dihydro-1-benzofuran-5-yl)-1-[(3-methyl-1,2-oxazol-4-yl)carbonyl]-2,3,10,10a-tetrahydroimidazo[2,1-g][1,7]naphthyridin-5(1H)-one.

17. The compound according to claim 1, wherein R$_1$ is a 5-6 membered heterocyclic ring containing nitrogen and/or oxygen.

18. A pharmaceutical composition comprising the compound, racemate, stereoisomer and/or salt thereof as defined in claim 1 and a pharmaceutically acceptable carrier.

19. The pharmaceutical composition of claim 18, wherein the compound is in a single stereoisomeric form.

20. The pharmaceutical composition of claim 19, wherein the single stereoisomeric form is represented by:

(I-i)

21. The pharmaceutical composition of claim 18, wherein the compound, racemate, stereoisomer and/or salt thereof is selected from the group consisting of:
10a-(4-chlorophenyl)-1-[(3-methyl-1,2-oxazol-4-y)carbonyl]-2,3,10,10a-tetrahydroimidazo[2,1-g][1,7]naphthyridin-5(1H)-one;
10a-(4-methoxyphenyl)-1-[(3-methyl-1,2-oxazol-4-y)carbonyl]-2,3,10,10a-tetrahydroimidazo[2,1-g][1,7]naphthyridin-5(1H)-one;
10a-(4-fluorophenyl)-1-[(3-methyl-1,2-oxazol-4-y)carbonyl]-2,3,10,10a-tetrahydroimidazo[2,1-g][1,7]naphthyridin-5(1H)-one;
10a-(4-fluoro-3-methylphenyl)-1-[(3-methyl-1,2-oxazol-4-yl)carbonyl]-2,3,10,10a-tetrahydroimidazo[2,1-g][1,7]naphthyridin-5(1H)-one;
10a-(3,4-difluorophenyl)-1-[(3-methyl-1,2-oxazol-4-yl)carbonyl]-2,3,10,10a-tetrahydroimidazo[2,1-g][1,7]naphthyridin-5(1H)-one;

10a-(2-chlorophenyl)-1-[(3-methyl-1,2-oxazol-4-yOcarbonyl]-2,3,10,10a-tetrahydroimidazo[2,1-g][1,7]naphthyridin-5(1H)-one;

10a-cyclohexyl-1-[(3-methyl-1,2-oxazol-4-yl)carbonyl]-2,3,10,10a-tetrahydroimidazo[2,1-g][1,7]naphthyridin-5(1H)-one;

10a-(4,4-difluorocyclohexyl)-1-[(3-methyl-1,2-oxazol-4-ypcarbonyl]-2,3,10,10a-tetrahydroimidazo[2,1-g][1,7]naphthyridin-5(1H)-one;

10a-(4-chlorophenyl)-1-{[3-(trifluoromethyl)-1,2-oxazol-4-yl]carbony11-2,3,10,10a-tetrahydroimidazo[2,1-g][1,7]naphthyridin-5(1H)-one; and 10a-(2,3-dihydro-1-benzofuran-5-yl)-1-[(3-methyl-1,2-oxazol-4-yl)carbonyl]-2,3,10,10a-tetrahydroimidazo[2,1-g][1,7]naphthyridin-5(1H)-one.

22. The pharmaceutical composition of claim 21, wherein the compound is in a single stereoisomeric form.

23. The pharmaceutical composition of claim 18, formulated as a liquid or powder for intranasal administration; or a tablet or capsule for oral administration; or a liquid for intravenous administration.

24. A process for preparing the compound of formula (I) according to claim 1, racemates, stereoisomers and/or salts thereof comprising the step of reacting a compound of formula (II):

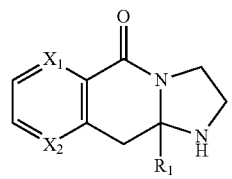

(II)

with a compound of formula (III):

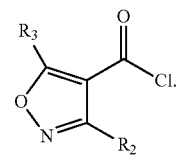

(III)

* * * * *

UNITED STATES PATENT AND TRADEMARK OFFICE
CERTIFICATE OF CORRECTION

| | |
|---|---|
| PATENT NO. | : 8,796,303 B2 |
| APPLICATION NO. | : 13/302975 |
| DATED | : August 5, 2014 |
| INVENTOR(S) | : Mayes et al. |

It is certified that error appears in the above-identified patent and that said Letters Patent is hereby corrected as shown below:

In the Claims

Column 52, lines 36-47: change the formula (I-i)

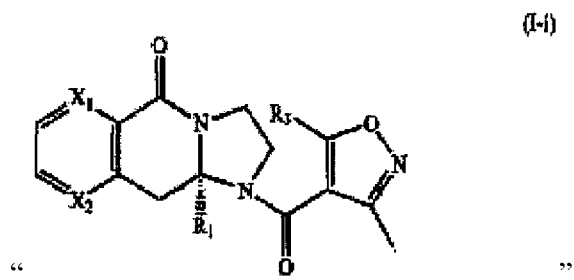

" "

to

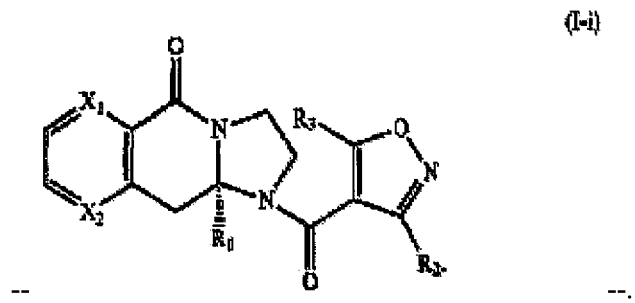

-- --.

Signed and Sealed this
Seventh Day of April, 2015

Michelle K. Lee
*Director of the United States Patent and Trademark Office*